United States Patent
Sherley

(10) Patent No.: US 9,733,236 B2
(45) Date of Patent: Aug. 15, 2017

(54) METHODS FOR DETERMINING THE EFFECT OF AN AGENT ON TISSUE STEM CELLS

(71) Applicant: James L. Sherley, Boston, MA (US)

(72) Inventor: James L. Sherley, Boston, MA (US)

(73) Assignee: James L. Sherley, Boston, MA (US)

( * ) Notice: Subject to any disclaimer, the term of this patent is extended or adjusted under 35 U.S.C. 154(b) by 0 days.

(21) Appl. No.: 14/682,384

(22) Filed: Apr. 9, 2015

(65) Prior Publication Data

US 2015/0293077 A1    Oct. 15, 2015

Related U.S. Application Data

(60) Provisional application No. 61/978,013, filed on Apr. 10, 2014.

(51) Int. Cl.
*G01N 33/50* (2006.01)

(52) U.S. Cl.
CPC ....... *G01N 33/5014* (2013.01); *G01N 33/502* (2013.01); *G01N 33/5073* (2013.01)

(58) Field of Classification Search
None
See application file for complete search history.

(56) References Cited

U.S. PATENT DOCUMENTS

| | | | |
|---|---|---|---|
| 7,824,912 B2 | 11/2010 | Sherley et al. | |
| 8,404,481 B2 | 3/2013 | Sherley et al. | |
| 2004/0071672 A1 | 4/2004 | Hogan | |
| 2010/0015710 A1 | 1/2010 | Jung et al. | |
| 2014/0219969 A1 | 8/2014 | Sasaki et al. | |

FOREIGN PATENT DOCUMENTS

| | | | | |
|---|---|---|---|---|
| WO | 2007/002228 A1 | 1/2007 | | |
| WO | WO 2013134649 A1 * | 9/2013 | ....... | G01N 33/57484 |

OTHER PUBLICATIONS

Gullo et al., "Prospective purification of a subpopulation of human synovial mesenchymal stem cells with enhanced thondro-osteogenic potency", Rheumatology, 52: 1758-1768 (2013).
Kalirai et al., "Uveal Melanoma Cell Lines Contain Stem-Like Cells That Self-Renew, Produce Differentiated Progeny and Survive Chemotherapy", Investigative Opthamology & Visual Science, 52(11): 8458-8466 (2011).

Prince et al., "Identification of a subpopulation of cells with cancer stem cells properties in head and neck squamous cell carcinoma", PNAS, 104(3): 973-78 (2007).
Hayflick, "The Limited In Vitro Lifetime of Human Diploid Cell Strains," Exp. Cell Res. 37:614-636 (1965).
Huh et al., "SACK-Expanded Hair Follicle Stem Cells Display Asymmetric Nuclear Lgr5 Expression With Non-Random Sister Chromatid Segregation", Sci. Rep. 1:176 (2011).
Lee et al., "Clonal Expansion of Adult Rat Hepatic Stem Cell Lines by Suppression of Asymmetric Cell Kinetics (SACK)", Biotech & Bioeng. 83(7):760-771 (2003).
Pare et al., "Biological Principals for Ex Vivo Adult Stem Cell Expansion", Current Topics in Developmental Biology 73:141-171 (2006).
Pare et al., "Culture Environment-Induced Pluripotency of SACK-Expanded Tissue Stem Cells", J. Biomed. Biotechnol. 2011:312457 (2011).
Pare et al., "Ex vivo Expansion of Human Adult Pancreatic Cells with Properties of Distributed Stem Cells by Suppression of Asymmetric Cell Kinetics", J. Stem Cell Res. Ther. 3(4):149 (2013).
Rambhatla et al., "Cellular senescence: ex vivo p53-dependent asymmetric cell kinetics", J. Biomed. Biotech. 1 (1):28-37 (2001).
Sherley et al., "Expression of the wild-type p53 antioncogene induces guanine nucleotide-dependent stem cell division kinetics", Proc. Natl. Acad. Sci. U.S.A. 92:136-140 (1995).
Sherley, "Advancing Renewable Normal Human Cell Assays for Drug Discovery," Drug Devel. Res. 74:127-137 (2013).
Sherley, "New cancer diagnostics and therapeutics from a ninth 'hallmark of cancer': symmetric self-renewal by mutated distributed stem cells", Expert Rev. Mol. Diagn. 13(8):797-810 (2013).
Todaro et al., "Quantitative Studies of the Growth of Mouse Embryo Cells in Culture and their Development into Established Lines", J. Cell Biol. 17:299-313 (1963).
Van Vliet, "Current Standing and Future Prospects for the Technologies Proposed to Transform Toxicity Testing in the 21st century", Altex 28(1):17-44 (2011).

* cited by examiner

*Primary Examiner* — Renee Claytor
*Assistant Examiner* — Sharon M Papciak
(74) *Attorney, Agent, or Firm* — Nixon Peabody LLP; Ronald I. Eisenstein; Candace M. Summerford

(57) ABSTRACT

Herein, we describe a direct in vitro method that identifies agents that are toxic against natural human tissue stem cells. We provide a novel schedule for culturing any cell population containing homologous tissue stem cells that allows the number and cell kinetics of tissue stem cells, transient cells, and terminally differentiated cells within the population to be monitored. Using the passage schedule together with determination of a growth curve for the population, one can determine whether or not an agent is toxic to tissue stem cells, or to transient cells and/or terminal cells. The same method can also be used to identify agents that act positively on tissue stem cells and the other specific cell types.

14 Claims, 19 Drawing Sheets

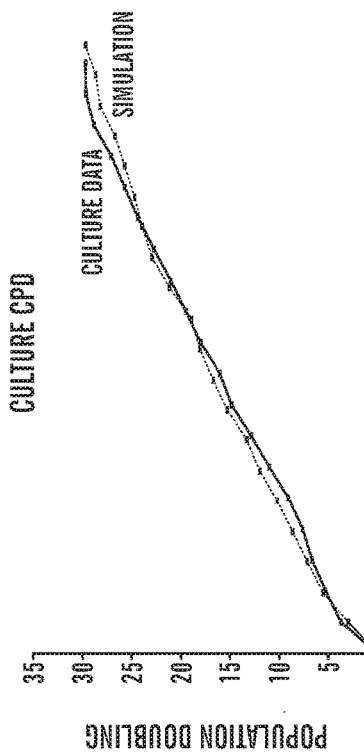
FIG. 13A
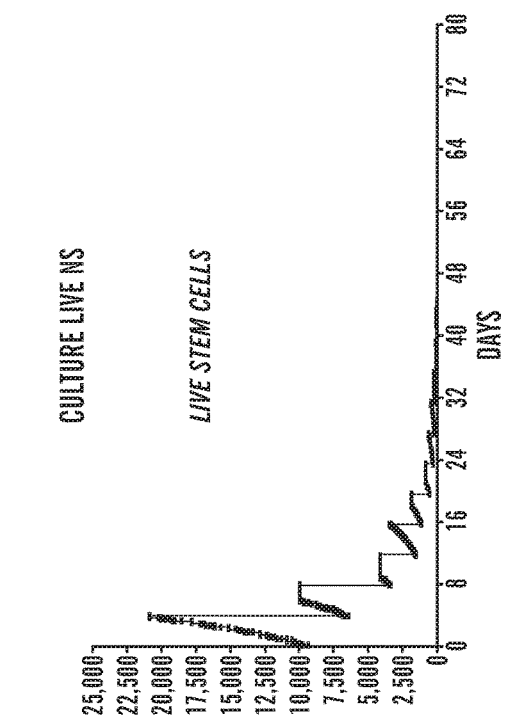
FIG. 13B
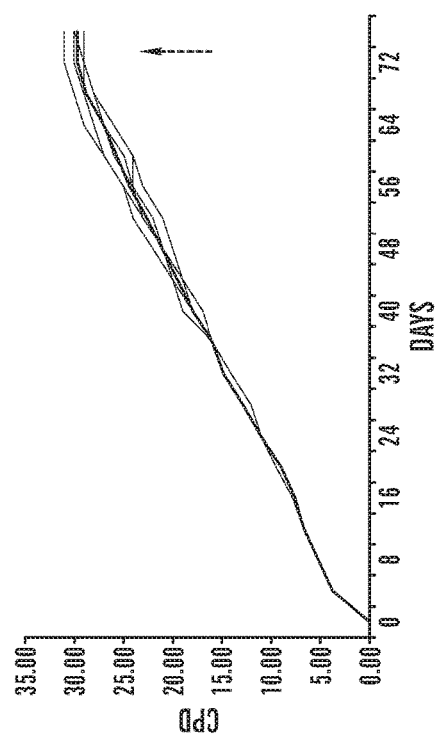
FIG. 13C
FIG. 13D

METHODS FOR DETERMINING THE EFFECT OF AN AGENT ON TISSUE STEM CELLS

CROSS-REFERENCE TO RELATED APPLICATIONS

This Application claims the benefit under 35 U.S.C. 119(e) of U.S. Provisional Application No. 61/978,013, filed Apr. 10, 2014, which is herein incorporated by reference in its entirety.

FIELD OF THE INVENTION

The present application is directed to methods for determining the effect of an agent on a heterogeneous population of cells comprising tissue stem cells, transient cells, and terminal cells, e.g. a toxic effect or a positive effect. The methods involve a unique culturing scheme where the combination of a cell passage schedule based upon a strict time interval, and the use of the same dilution in each passage such that the cell culture experiences a rapid decline in cell number, enables one to monitor the number and cell kinetics of all three types of cells, i.e. tissue stem cells, transient cells, and terminal cells. The cell population using such schedule reaches a point of containing only terminally differentiated cells (a lack of cell division) faster than the recommended passaging schedules for primary (freshly isolated) or cultured cells that contain tissue stem cells, transient cells, and terminal cells. In particular, the culture has cumulative population doublings that allow for the ability to monitor the number and cell kinetics of all three cell types within the heterogeneous population of cells.

BACKGROUND OF THE INVENTION

Because tissue stem cells are responsible for renewing and repairing human tissues, drugs that interfere with their function or cause their death are particularly toxic. FIG. 1 illustrates the universal, hierarchal human tissue cell kinetics architecture. Tissue stem cells (NS) subtend tissue turnover units comprised of many dividing and differentiating transient amplifying cells (NT) and terminally differentiated cells (NT-Terminal). As differentiated terminal cells age, expire, and are loss from a given tissue, they are replaced by the division of transient cells, which are in turn replaced by the division of the resident tissue stem cells.

Despite the importance of tissue stem cells in adverse toxic drug effects, currently there are no pre-clinical assays for tissue stem cell toxicity that do not require animals. Even animal testing is indirect, as it involves evaluating the pathological consequences of tissue stem cell toxicity (e.g., tissue dysplasia, anemia). Also, animal models are known to be poor predictors for tissue stem cell toxicity in humans.

A number of factors conspire to cause the current lack of direct pre-clinical assays for tissue stem cell toxicity. Because of their unique place in the universal cell kinetics hierarchy of human tissues, tissue stem cells are a minute fraction of any human tissue cell preparation. As a result, they have proven difficult to isolate in sufficient number or purity to establish reliable assays. For the same reason, no biomarkers for tissue stem cells are available with sufficient specificity to quantify tissue stem cells for drug toxicity testing.

Toxicity against tissue stem cells is one of the most intolerable forms of drug toxicity, which can lead to drug candidate failure late in expensive clinical trials, and potentially after marketing. However, the only currently available pre-clinical tests for detecting human tissue stem cell toxicity are animal models. Such tests are expensive and often do not faithfully predict toxic effects in human patients

SUMMARY OF THE INVENTION

We have identified an in vitro method that uses a distinct schedule for passaging a population of cells comprising tissue stem cells, transient cells and terminal cells, by which agents that are toxic against natural human tissue stem cells present in the population can be discerned. The method is suitable for culturing any heterogeneous population of cells comprising homologous tissue stem cells. The cell kinetics data derived from the schedule allows determination of whether an agent is toxic to tissue stem cells and/or is toxic to the other specific cell types that compose the natural tissue cell hierarchy (FIG. 1), i.e. transient cells or terminal cells. The same method can also be used to identify agents that act positively on tissue stem cells and the other specific cell types. For example, an increase in growth of or number of tissue stem cells.

Accordingly, one aspect of the invention provides methods of culturing a heterogeneous population of cells that allows for determination of the effect of an agent on the tissue stem cells. The method comprises step a) culturing a heterogeneous population of cells comprising tissue stem cells, transient cells and terminally differentiated cells; and step b) performing sequential passages of the cultured cells of step a) based on a specific time interval for passage rather than, for example, passage based on confluency (cell density). The cells are sequentially passaged at a given time interval using the same dilution factor at each passage such that the cells do not reach more than 50% confluency at the time for passage. This results in a cell culture that rapidly declines in cell number (e.g. a culture where the cell number at the time of passage starts declining within 4 passages, within 5 passages, within 6 passages, within 7 passages, or within 10 passages). An important feature is that the culture declines in cell number. In one embodiment, the cells are sequentially passaged until at least two passages are performed without any increase in cell number in the culture prior to next passage. In an alternative embodiment, the cells are sequentially passaged until a culture at the time of passage has less than 40%, less than 30%, less than 20%, or less than 10%, of the original starting cell number (e.g. prior to containing only terminally differentiated cells, i.e. prior to two times passage where there is no increase in cell number at the time of passage). The decline in the cell number in the heterogeneous culture allows the number and cell kinetics of all three cell types in the heterogeneous population to be monitored, (i.e. tissue stem cells, transient cells and terminally differentiated cells).

In another aspect, the methods for culturing a heterogeneous population of cells comprising tissue stem cell, transient cells and terminal cells, described above, are used to determine the effect of a test agent on the population of cells. The methods comprise culturing a heterogeneous population of cells as described in step a} and step b) of the above paragraph. However, in this aspect, the heterogeneous population of cells is contacted with a test agent prior to, or during, the sequential passage as described in steps a) and b) of above paragraph. To determine the effect of the test agent, the cell number of the culture is determined at each sequential passage so that the number of population doubling versus time of passage can be plotted in order to obtain a growth curve for the heterogeneous population. The growth curve of the cells contacted with the test agent is then compared to a control culture that has not been contacted with the agent, wherein a deviation of the growth curve with the agent from the control growth curve indicates the agent has either a toxic or a positive effect on tissue stem cells, transient cells, or terminal cells.

For example, when the deviation of the curve is due to a lower amount population doublings early in the growth curve and to a faster time to reach the two passages that are performed without any increase in cell number (See e.g. FIG. 7), the agent is toxic to tissue stem cells. When the deviation of the curve is due to a lower amount population doublings late in the growth curve, and the time to reach the two passages that are performed without any increase in cell number in the culture is similar to the control (See e.g. FIG. 9), the agent is toxic to transient cells. In addition, when the deviation of the curve is due to a higher amount of population doublings in the middle of the growth curve, and the time to reach the least two passages that are performed without any increase in cell is similar to the control (See e.g. FIG. 12), the agent has a positive effect on tissue stem cells. In one embodiment of this aspect, the positive effect is an increase in tissue stem cell number, viability, or function. In another embodiment of this aspect, the toxic effect is a decrease in tissue stem cell number, viability, or function.

In one embodiment of each of the aspects above, there is a decline in the cell number of the culture at the time of passage within six sequential passages, as compared to the cell number at the time of a prior passage. In one embodiment of each of the aspects above, there is a decline in the cell number of the culture at the time of passage, as compared to the cell number at the time of a prior passage, within five sequential passages. In one embodiment of each of the aspects above, there is a decline in the cell number of the culture at the time of passage, as compared to the cell number at the time of a prior passage, within 4 sequential passages.

In some embodiments of each of the aspects above, the period of time until at least two passages are performed without any increase in cell number in the culture is less than 100 days, or less than 90 days, or less than 80 days.

In some embodiments of each of the aspects above, the starting cell culture of step a) has a population cell number that corresponds to 200,000 cells in a 75 cm$^2$ plate or flask, 65,000 cells in a 25 cm$^2$ plate or flask, or 22,000 cells in a 8.3 cm$^2$ plate or flask. In some embodiments, the starting cell number of the culture is less than 50,000 cells/cm2, less than 10,000 cells/cm$^2$, or less than 7,000 cells/cm$^2$. In certain embodiments of each of the above aspects, the cell concentration is greater than 2,600 cells/cm$^2$.

In some embodiments of each of the aspects above, the specific time interval is every 108 hours, every 96 hours, every 72 hours, or every 48 hours.

In some embodiments of each of the aspects above, the dilution factor is 1:2, is 1:3, is 1:5, or is 1:10.

In some embodiments of each of the aspects above, the cell number at the two passages that are performed without any increase in cell number has declined to less than 40% of the cell number in step a). In some embodiments of each of the aspects above, the cell number at the two passages that are performed without any increase in cell number has declined to less than 30% of the cell number in step a). In some embodiments of each of the aspects above, wherein the cell number at the two passages that are performed without any increase in cell number has declined to less than 20% of the cell number in step a). In some embodiments of each of the aspects above, the cell number at the two passages that are performed without any increase in cell number has declined to less than 10% of the cell number in step a).

In some embodiments of each of the aspects above, the percentage of tissue stem cells in the population is less than 5%.

In some embodiments of each of the aspects above, the heterogeneous population of cells is obtained from organ tissue.

In some embodiments of each of the aspects above, the heterogeneous population of cells is obtained from diseased tissue. For example, non-limiting examples of diseased tissue include virally infected tissue, or tissues having a genetic defect.

In some embodiments of each of the aspects above, the heterogeneous population of cells are infected, transformed or transfected to produce a heterogeneous population of cells that are models of a specific disease. For example the cells may be transformed with a bacterial plasmid, transfected with viral vectors, or infected with viruses to mimic a disease state thereby allowing assessment of the effect of a test agent on tissue stem cells that are associated with disease. In certain embodiments, nucleic acid is introduced to express proteins related to the disease. In certain embodiments, nucleic acid is introduced that in inhibits gene expression, e.g. RNAi or antisense.

Also provided, is a method of culturing a heterogeneous population of cells that allows for determination of the effect of an agent on the tissue stem cells within the heterogeneous population comprising: performing sequential passaging of a heterogeneous population of cells comprising tissue stem cells, transient cells, and terminally differentiated cells, in a manner that the cells in culture cease to divide within a period of 100 days (within 90, 80, 60, days), thereby allowing the number and cell kinetics of tissue stem cells, transient cells and terminally differentiated cells to be monitored within the population. In one embodiment, the cell number of the culture begins to decline at the time of passage within six sequential passages, (or within 5 sequential passages, or within 4 sequential passages) as compared to the cell number present at the time of a prior passage. In one embodiment, the cells are sequentially passaged until the culture at the time of passage has less than 40%, less than 30%, less than 20%, or less than 10%, of the original starting cell number.

BRIEF DESCRIPTION OF THE DRAWINGS

FIGS. 13A to 13D are graphs showing experimental and probabilistic stem cell kinetics (PSCK) simulation of WI-38 human lung fibroblast serial culture data. FIG. 13A. Experimental data set, n=6. Mean CPD (cumulative population doublings; bold black line). FIG. 13B. A single PSCK simulation versus the experimental mean CPD. FIG. 13C. A replicate (n=10) simulation compared to the experimental mean CPD data (bold black line). FIG. 13D. Deconstructed live stem cell number in WI-38 serial cultures. Arrows, indicate the times of the characteristic culture growth arrest.

FIG. 14A. Experimental data showing the ability of xanthosine to increase the proliferative rate and extent of human liver stem cell serial cultures. FIG. 14B. PSCK simulation of the experimental data. FIG. 14C. Computer simulation deconstruction of live stem cell number. FIG. 14D. Computer simulation deconstruction of the number of symmetric self-replication divisions by liver tissue stem cells.

FIG. 15A. Control condition (drug-free) simulation of human lung cell serial culture CPD (black line for A-D). FIG. 15B. Simulated effect of a transient cell-specific toxic drug at IC90. FIG. 15C. Simulated effect of a tissue stem cell-specific toxic drug at IC90. FIG. 15D. Simulated effect of a tissue stem cell-specific toxic drug at IC50.

FIG. 16A. Control drug-free condition. FIG. 16B. Transient cell-specific toxic drug at IC90. FIG. 16C. Tissue stem cell-toxic drug at IC90. FIG. 16D. Tissue stem cell-toxic drug at IC50.

DETAILED DESCRIPTION OF THE INVENTION

We have now invented a method of culturing a heterogeneous population of cells comprising tissue stem cells, transient cells, and terminal cells that enables the kinetics of all three culture types to be monitored, e.g. to determine the effect on an agent on each of the three cell types. In certain embodiments, agents are assessed for a toxic (negative) effect of an agent on tissue stem cells. In certain embodiments, agents are assessed for a positive effect of an agent on tissue stem cells, e.g. agents that increase cell growth, viability, or cell number of tissue stem cells are desirable.

The present application is directed to methods for determining the effect of an agent on a heterogeneous population of cells comprising tissue stem cells, transient cells, and terminal cells, e.g. a toxic effect or a positive effect. The methods involve a unique culturing scheme where the combination of a cell passage schedule based upon a time interval, and the use of the same dilution in each passage such that the cell culture experiences a rapid decline in cell number, and reaches the point of containing only terminally differentiated cells (a lack of cell division) faster than the recommended passaging schedules for primary (freshly isolated) or cultured cells containing tissue stem cells, transient cells, and terminal cells. In particular, the culture has cumulative population doublings that allow for the ability to monitor the number and cell kinetics of all three cell types within the heterogeneous population of cells.

Figure 1:
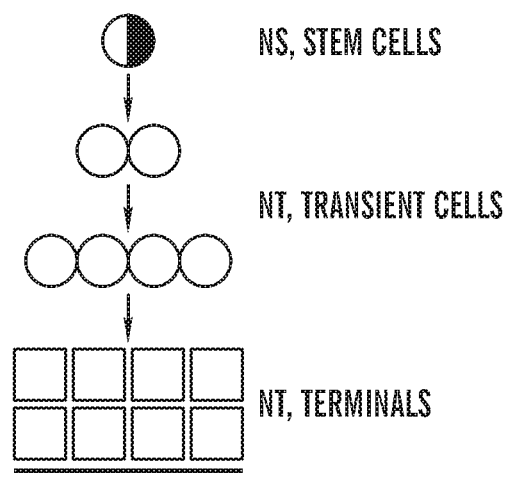
FIG. 1 shows a schematic of the three types of cells present in tissue and their hierarchal cell kinetics architecture.

Embodiments of the invention circumvent the longstanding barriers of isolation and identification of tissue stem cells. It does so applying tested drugs to directly treat tissue stem cells in the context of fresh or previously cultured human tissue cell preparations. The rate-limiting factor for the long-term cell production of any mammalian cell culture is directly related to the number, viability, and health of tissue stem cells in the culture. As shown in FIG. 1, since all transient cells progress eventually to non-dividing terminal cells, continued cell production by a mammalian cell culture absolutely depends on the continued presence of tissue stem cells in the culture.

Because of the asymmetric self-renewal of tissue stem cells, if a cell culture is serially passaged, cell production eventually stops because of the consequential dilution of the tissue stem cell number in the culture to zero (2-7). Conventional serial passaging involves growing a cell culture until the culture vessel is replete with cells, e.g. greater than 70%, greater than 80%, or more confluency. When replete, the cells are harvested; and a fixed fraction of the harvested cells is transferred to a new culture vessel. The new culture is allowed to grow until replete again, and the dilution process is performed again. There are well known examples of such serial passaging schedules for both human cells (8)

and rodent cells (9). In the case of human tissue cell cultures, this serial process inevitably leads to a complete stoppage in new cell production. At the endpoint, the cultures are predicted to contain only terminal cells. This outcome results from first dilution of tissue stem cell number to zero, followed by completion of the remaining transient cells differentiation and production of terminal cells (2).

We have discovered that by altering the typical serial passage schedule to create a culture that declines, it is possible to relate the total cell output of a culture containing tissue stem cells to the relative number, viability, and quality of tissue stem cells present. In embodiments of the invention the culturing schedule does not wait for cell cultures to become replete with cells, (e.g. greater than or equal to 80% confluency). Instead, the specified schedule of passaging is maintained no matter what cell number is obtained at the end of each growth interval. Even when the cell number appears fixed, the dilution is continued until there are at least two successive passage intervals without any increase in cell number. The cell kinetics of such a schedule can be related directly to the number, viability, and health of tissue stem cells during the duration of the serial passaging. It can also be related to the cell kinetics activities of transient cells and terminal cells.

By comparing the cell kinetics (i.e., total cell number versus time or cumulative cell population doublings versus time) of control culture data to drug-treated culture data, it is possible to determine whether an agent is toxic to, is neutral, or has a positive effect on, tissue stem cells, transient cells, terminal cells, or any and all combinations of the three cell types. Control culture data are representative of the same heterogeneous population of cells not treated with the drug, i.e. the test agent, e.g. the same heterogeneous population of cells is split into a control group and a test group for a control culture and a test culture, which are treated the same except for the presence of dug being present in the test culture and absence of drug in the control culture. Alternatively, the control culture data is a computer-simulated curve determined using the probabilistic stem cell kinetics (PSCK; 6,10) model (See for example FIGS. 4-12) of asymmetric and symmetric kinetics, the model being representative of the kinetics of the same population of cells being tested against the agent.

The methods of the invention can be used to easily identify agents that are toxic to tissue stem cells without the need for tissue stem cell isolation and purification. Conversely, it of course follows that the same methods can also be used to identify agents that act on tissue stem cells, transient cells, or terminal cells to increase their division, viability, or function.

Embodiments of the invention provide methods of culturing a heterogeneous population of cells that allows for determination of the effect of an agent on the tissue stem cells. The method comprises a) culturing a heterogeneous population of cells comprising tissue stem cells, transient cells and terminally differentiated cells; and b) performing sequential passages of the cultured cells of step a) based on a specific time interval for passage rather than passage based on cell density. The cells are sequentially passaged at the specific time interval using the same dilution factor at each passage such that the cells do not reach more than 50% confluency at the time for passage. This results in a cell culture that rapidly declines in cell number (e.g. that starts declining within 4 passages, within 5 passages, or within 10 passages). The cells are sequentially passaged until at least two passages are performed without any increase in cell number in the culture prior to next passage. The decline in the cell number in the culture allows the number and cell kinetics of all three cell types in the heterogeneous population to be monitored, (i.e. tissue stem cells, transient cells and terminally differentiated cells).

In certain embodiments, the period of time until at least two passages are performed without any increase in cell number in the culture is less than 100 days, less than 90 days, or less than 80 days. Typical passage of heterogeneous cell populations involve passaging based on confluency of the cell culture, because cells prefer to be close to one another for optimal growth conditions.

In certain embodiments of the above aspects, the period of time until at least two passages are performed without any increase in cell number in the culture is less than 100 days, less than 90 days, or less than 80 days. Typical passage of heterogeneous cell populations involve passaging based on confluency of the cell culture as cells prefer to be close to one another for optimal growth conditions.

The time interval for passage and the dilution factor can vary dependent upon the starting cell population in order to obtain a decline in cell number of the culture at the time of passage, for example, within 4 sequential passages, within 5 sequential passages, within 6 sequential passages, within sequential 7 passages, or within 10 sequential passages as compared to the cell number present at the time of a prior passage. The combination is such that the cell number in the culture at the time of passage continues to decline after reaching maximum cell number, for example after reaching maximum cell number at the time of sequential passage number 3, sequential passage number 4, sequential passage number 5, or sequential passage number 7.

In one embodiment, the specific time interval used for each sequential passage of the cell culture (i.e. of a heterogeneous population of cells comprising tissue stem cells, transient cells and terminal cells) is every 108 hours. In one embodiment, the specific time interval used for each sequential passage of the cell culture is every 96 hours. In one embodiment, the specific time interval used for each sequential passage of the cell culture every 72 hours. In one embodiment, the specific time interval used for each sequential passage of the cell culture is every 48 hours.

In certain embodiments the dilution factor at the given time interval is 1:2, or 1:3, or 1:5, or 1:10. It should be noted that any combination of time interval and dilution factor can be used as long as during the time of passage the culture does not reach more than 50% confluency at any passage. This method ensures that the culture will eventually present with a declining cell number and containing only terminally differentiated cells (lack of cell division) within a period of time less than 100 days, for example within 100 days, 90 days, 80 days, or 70 days. The recommended passage schedule based on confluency for a heterogeneous population of cells comprising tissue stem cell, transient cells and terminal cells typically results in a culture that contains only terminally differentiated cells (lack of cell division) greater than 100 days, e.g. 150 days. In addition, the recommended passage schedule based on confluency for a heterogeneous population of cells comprising tissue stem cell, transient cells and terminal cells results in a population of cells throughout the 80, 90 or 100 days, does not allow for discerning the number and cell kinetics of the three cell types, tissue stem cells, transient cells, and terminal cells.

We have determined that, if one monitors the population growth kinetics in a declining culture, the number and cell kinetics of all three cell types can be discerned. In certain embodiments, the cell number at the two passages that are performed without any increase in cell number has declined to less than 40% of the starting cell number of the heterogeneous cell culture. In one embodiment, the cell number at the two passages that are performed without any increase in cell number has declined to less than 30% of the starting cell number of the heterogeneous cell culture. In one embodiment the cell number at the two passages that are performed without any increase in cell number has declined to less than 20% of the starting cell number of the heterogeneous cell culture. In one embodiment, the cell number at the two passages that are performed without any increase in cell number has declined to less than 10% of the starting cell number of the heterogeneous cell culture.

As mentioned above, the starting number of cells can vary. However, it should be that the cells do not reach more than 50% confluency at any time interval of passage to ensure a rapid decline in cell culture and the ability to obtain a kinetic growth curve during the decline phase. Examples of appropriate cell numbers include, for example, 200,000 cells in a 75 $cm^2$ plate or flask, 65,000 cells in a 25 $cm^2$ plate or flask, or 22,000 cells in a 8.3 $cm^2$ plate or flask. In some embodiments, the starting cell number of the culture is less than 50,000 cells/$cm^2$, less than 10,000 cells/$cm^2$, or less than 7,000 cells/$cm^2$. In certain embodiments, the cell concentration is greater than 2,600 cells/$cm^2$.

In one embodiment, a method of culturing a heterogeneous population of cells that allows for determination of the effect of an agent on the tissue stem cells within the heterogeneous population is provided that comprises performing sequential passaging of a heterogeneous population of cells comprising tissue stem cells, transient cells, and terminally differentiated cells, in a manner that the cells in culture cease to divide within a period of 100 days (or within 90, within 80, or within 60 days), thereby allowing the number and cell kinetics of tissue stem cells, transient cells and terminally differentiated cells to be monitored within the population. The culture ceases to divide earlier than observed with traditional passaging schedules because the culture is in a decline phase throughout a majority of the passages. It is the decline stages that allow all three kinetic cell types to be monitored for number and cell kinetics. In one embodiment, the cell number of the culture begins to decline at the time of passage within six sequential passages, (or within 5 sequential passages, or within 4 sequential passages) as compared to the cell number present at the time of a prior passage. In one embodiment, the cells are sequentially passaged until the culture at the time of passage has reached less than 40%, less than 30%, less than 20%, or less than 10%, of the original starting cell number.

In methods of the invention, the starting population is a heterogeneous population of cells. As used herein a "heterogeneous population of cells" is a cell population that contains three kinetic cell types, tissue stem cells, transient cells and terminal cells. These cells exhibit the kinetic hierarchy as depicted in FIG. 1. In certain embodiments, the percentage of tissue stem cells in the population is less than 5%, less than 10%, less than 20%, or less than 30%.

As used herein, the term "tissue stem cell" refers to somatic stem cells that are derived from adult tissues and herein are sometimes referred to as simply as stem cells, or adult stem cells. Somatic stem cells include cells in tissues that divide to produce the differentiated cells of the tissue, while maintaining their own undifferentiated stem cell properties. The term "tissue stem cell" is used to refer to any multipotent or unipotent stem cell derived from non-embryonic tissue, including fetal, juvenile, and adult tissue. Tissue stem cells have been isolated from a wide variety of adult tissues including blood, bone marrow, brain, olfactory epithelium, skin, pancreas, skeletal muscle, and cardiac muscle. Each of these tissue stem cells can be characterized based on gene expression, factor responsiveness, tissue reconstitution, chromosome segregation, and cell culture kinetics. Exemplary tissue stem cells include liver stem cells, hair follicle stem cells, neural stem cells, neural crest stem cells, mesenchymal stem cells, hematopoietic stem cells, and pancreatic stem cells. As indicated above, tissue stem cells have been found resident in virtually every tissue. "Adult stem cell," "somatic stem cell," and "tissue stem cell" are used interchangeably.

The term "multipotent" when used in reference to a "multipotent cell" refers to a cell that is able to differentiate into some but not all of the cells derived from all three germ layers; or into multiple cell types that constitute a single type of tissue or organ. Thus, a multipotent cell is a partially differentiated cell with respect to the earliest embryonic cells. Multipotent cells are well known in the art, and examples of multipotent cells include tissue stem cells, such as for example, hematopoietic stem cells, neural stem cells, hair follicle stem cells, liver stem cells, etc. Multipotent means a stem cell can form many types of cells in a given lineage, but not cells of other lineages. For example, a multipotent blood stem cell can form the many different types of blood cells (red, white, platelets, etc.), but it cannot form neurons; cardiovascular progenitor cell differentiate into specific mature cardiac, pacemaker, smooth muscle, and endothelial cell types; pancreas-derived multipotent progenitor colonies produce cell types of pancreatic lineage (cells that produces insulin, glucagon, amylase or somatostatin) and neural lineage (cells that are morphologically neuron-like, astrocytes-like or oligodendrocyte-like). As described above, the tissue stem cell can be multipotent or unipotent (produces one differentiated cell type like limbal stem cells that make corneal epithelium cells).

Somatic stem cells (tissue stem cells) predominantly divide by asymmetric cell kinetics. While somatic stem cells also undergo limited symmetric divisions (that produce two identical stem cells) in developing adult tissues, such symmetric kinetics are restricted to periods of tissue expansion and tissue repair. Inappropriate symmetric somatic stem cell divisions evoke mechanisms leading to apoptosis of duplicitous stem cells (Potten and Grant, The relationship between ionizing radiation-induced apoptosis and stem cells in the small and large intestine. *British J. of Cancer* 78, 993-1003 (1998). Some stem cells may also lie dormant for long periods before initiating division in response to specific developmental cues, as in reproductive tissues like the breast. However, the predominant cell kinetics state of somatic stem cells is asymmetric (Cairns, Mutation selection and the natural history of cancer. *Nature* 255, 197-200. (1975); Poldosky, Regulation of intestinal epithelial proliferation: a few answers, many questions. *Am. J. Physiol.* 264, G179-G186 (1993); and Loeffler and Potten, Stem cells and cellular pedigrees—a conceptual introduction. *In Stem Cells*, C. S. Potten, ed., San Diego, Calif.: Harcourt Brace & Co., pp. 1-28 (1997)).

During asymmetric cell kinetics, one daughter cell divides with the same kinetics as its stem cell parent, while the second daughter gives rise to a differentiating non-dividing cell lineage. The second daughter may differentiate immediately; or depending on the tissue, it may undergo a finite number of successive symmetric divisions to give rise to a larger pool of differentiating cells. The second daughter and its dividing progeny are called transit cells (Loeffler and Potten, Stem cells and cellular pedigrees—a conceptual introduction. *In Stem Cells*, C. S. Potten, ed., San Diego, Calif.: Harcourt Brace & Co., pp. 1-28 (1997)), herein referred to as "transient cells". Transit cell divisions ultimately result in mature, differentiated, terminally arrested cells, herein referred to as "terminally differentiated cells", also known as "terminal cells." In tissues with high rates of cell turnover, the endpoint for differentiated terminal cells is programmed cell death by apoptosis.

Asymmetric cell kinetics evolved in vertebrates as a mechanism to insure tissue cell renewal while maintaining a limited set of stem cells and constant adult body mass. Mutations that disrupt asymmetric cell kinetics are an absolute requirement for the formation of a clinically significant tumor mass (Cairns, Mutation selection and the natural history of cancer. Nature 255, 197-200. (1975)). In many ways, asymmetric cell kinetics provide a critical protective mechanism against the emergence of neoplastic growths that are life threatening.

In culture, continued asymmetric cell kinetics of explanted cells are a major obstacle to their expansion in vitro. Ongoing asymmetric cell kinetics results in dilution and loss of an initial relatively fixed number of stem cells by the accumulation of much greater numbers of their terminally differentiating progeny. If a sample includes both exponentially growing cells as well as somatic stem cells, the multiplication of the exponentially growing cells will rapidly overwhelm the somatic stem cells, leading to their dilution.

One regulator of asymmetric cell kinetics is the p53 tumor suppressor protein. Several stable cultured murine cell lines have been derived that exhibit asymmetric cell kinetics in response to controlled expression of the wild-type murine p53 (Sherley, Guanine nucleotide biosynthesis is regulated by the cellular p53 concentration. *J. Biol. Chem.* 266, 24815-24828. (1991); Sherley et al, Expression of the wild-type p53 antioncogene induces guanine nucleotide-dependent stem cell division kinetics, *Proc. Natl. Acad. Sci. USA* 92, 136-140. (1995); Liu et al., Comparison of Bax, Waf1, and IMP dehydrogenase regulation in response to wild-type p53 expression under normal growth conditions. *J. Cellular Physiology* 177, 364-376 (1998); and Rambhatla et al., Cellular senescence: ex vivo p53-dependent asymmetric cell kinetics. *J. Biomed. Biotech.* 1, 28-37. (2001).

Cell Culture

The heterogeneous cell population of the present invention may be isolated from tissue of an adult mammal, preferably a human. Cells can be obtained from donor tissue, such as donor skin or other organs, by dissociation of individual cells from the connecting extracellular matrix of the tissue. Tissue is removed using a sterile procedure, and the cells are dissociated using any method known in the art including treatment with enzymes such as trypsin, collagenase, and the like, or by using physical methods of dissociation such as with a blunt instrument. The heterogeneous cell population may also be obtained from bodily fluids; including, but not limited to, blood, umbilical cord, spinal fluid, pleural fluid, and lymphatic fluid.

In certain embodiments, the heterogeneous population of cells is obtained from organ tissue. Tissue can be obtained from any organ, including but not limited to: organs of the musculoskeletal skeletal system, e.g. bone, cartilage, fibrous joints, cartilaginous joints, synovial joint, muscle, tendon, or diaphragm; organs of the cardiovascular system, e.g. artery, vein, lymphatic vessel, or heart; organs of the lymphatic system, e.g. primary (bone marrow, thymus), secondary (spleen and lymph node), CNS equivalent (cerebral spinal system); organs of the nervous system, e.g. brain, spinal cord, nerve; organs of the sensory system, e.g. ear, cochlea, eye; organs of the integumentary system, e.g. skin, subcutaneous tissue, breast (mammary gland), hair; organs of the immune system, e.g. myeloid (myeloid immune system) or lymphoid (lymphoid immune system); organs of the respiratory system, e.g. upper (e.g. nose, nasopharynx, larynx) or lower system (e.g. trachea, bronchus, lung); organs of the digestive system, e.g. mouth (salivary gland, tongue), upper gastrointestinal (GI; oropharynx laryngopharynx, esophagus, stomach), lower GI (e.g. small intestine, appendix, colon, rectum, anus) or accessory GI (e.g. liver, biliary tract, pancreas); organs of the urinary system, e.g. genitourinary system: e.g. kidney, ureter, bladder, and urethra; organs of the reproductive system, female (uterus, vagina, vulva, ovary, placenta) male (scrotum, penis, prostate, testicle, seminal vesicle); organs of the endocrine system, e.g. pituitary, pineal gland, thyroid, parathyroid, adrenal or islets of Langerhans. Cells can be of the mesoderm, endoderm, or ectoderm origin.

Also useful in methods of the invention are cell culture systems that contain a heterogeneous population of cells including stem cells, transient cells, and terminally differentiated cells. Such systems are known to those of skill in the art and include, but are not limited to those described in, U.S. patents and publications 20140193910; U.S. Pat. Nos. 8,759,098; 8,404,481; 7,883,891; 7,867,712; 7,824,912; 7,655,465; 7,645,610, and 20030133918; which are herein incorporated by reference in their entirety. Thus, known in the art are cell culture system for all types of tissues including, but not limited to, human liver, skin, heart, kidney, lung, hematopoietic, hair follicle, muscle, and pancreatic cells.

In certain embodiments, the heterogeneous population of cells is obtained from diseased tissue. For example, non-limiting examples of diseased tissue include virally infected tissue, or tissues having a genetic defect that results in disease, or e.g. cancerous tissue, or e.g., many common diseases and disorders like heart failure, diabetes, autism, stroke, or kidney disease. Diseased tissue can be isolated to obtain the heterogeneous population of cells by isolating tissue from a subject having the disease or disorder of interest. In certain embodiments, the heterogeneous population of cells is obtained from a patient having cancer, e.g. bone marrow cancer, leukemia, etc., or cells isolated from a tumor, or growth.

In an alternative embodiment, a heterogeneous population of cells is infected, transformed, or transfected to produce a heterogeneous population of cells that is a model of a specific disease. For example the cells may be transformed with a bacterial plasmid, transfected with viral vectors, or infected with viruses, in order to mimic a disease state, thereby allowing assessment of the effect of a test agent on tissue stem cells that are associated with disease. Cells infected with any virus can be studied, including but not limited to the following viruses: Retroviruses, Human immunodeficiency virus (HIV), or Cytomegalovirus, Adenoviruses, Herpesviruses, Poxviruses, Parvoviruses, Reoviruses, Picornaviruses, Togaviruses, Orthomyxoviruses, and Rhabdoviruses etc.

In certain embodiments, nucleic acid is introduced to express proteins related to the disease. In certain embodiments, a nucleic acid associated with a disease state is introduced, e.g. having a genetic mutation that causes disease; non-limiting examples include Familial hypercholesterolemia, Polycystic kidney disease, Neurofibromatosis type, Hereditary spherocytosis, Marfan syndrome, Huntington's disease; ALS, Sickle cell anemia; Cystic fibrosis; Tay-Sachs disease; Phenylketonuria; Mucopolysaccharidoses; Mucopolysaccharidoses; Lysosomal acid lipase deficiency; Glycogen storage diseases; Galactosemia; Duchenne muscular dystrophy; and Hemophilia In certain embodiments, a nucleic acid is introduced that inhibits gene expression, e.g. RNAi or antisense RNA, thereby modeling the disease of interest. As used herein, the term "RNAi" refers to any type of interfering RNA, including but are not limited to, siRNA, shRNA, endogenous microRNA and artificial microRNA. Methods of making RNAi are well known to those of skill in the art, e.g. See e.g. Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), and Bartel et al. Cell 116:281-297 (2004).

Methods of transfection, infection, and transformation are well known to those of skill in the art, for example as described in; Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), which are herein incorporated by reference in their entirety.

As used herein, the term "passage" refers to diluting the cell culture, whether it be on plates, or in suspension, and re-culturing (re-plating) the diluted cells. For example, for passage of cells, the cells are removed from their tissue culture dish (e.g. by treatment with trypsin) or flask and diluted so that they can be re-plated (on plates or in a flask) and allowed to continue to grow.

Any medium can be used that is capable of supporting cell growth, including HEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. Serum can contain xanthine, hypoxanthine, or other compounds that enhance guanine nucleotide biosynthesis, although generally at levels below the effective concentration to suppress asymmetric cell kinetics. In one embodiment, for the cell culture the medium and serum contain levels below the effective concentration to suppress asymmetric cell kinetics. In one embodiment, the culture medium is a defined culture medium comprising a mixture of DMEM, F12, and a defined hormone and salt mixture.

The culture medium can be supplemented with a proliferation-inducing growth factor(s). As used herein, the term "growth factor" refers to a protein, peptide or other biological molecule having a growth, proliferative, differentiating, or trophic effect on stem cells or other cell types. Growth factors that may be used include any trophic factor that promotes cells to proliferate, including any molecule that binds to a receptor on the surface of the cell to exert a trophic, or growth-inducing effect on the cell. Examples of proliferation-inducing growth factors include, but are not limited to, EGF, amphiregulin, acidic fibroblast growth factor (aFGF or FGF-1), basic fibroblast growth factor (bFGF or FGF-2), transforming growth factor alpha (TGF.alpha.), and combinations thereof. Growth factors are usually added to the culture medium at concentrations ranging between about 1 fg/ml to 1 mg/ml. Concentrations between about 1 to 100 ng/ml are usually sufficient. Simple titration experiments can be easily performed to determine the optimal concentration of a particular growth factor. In one preferred embodiment, epidermal growth factor is used.

In addition to proliferation-inducing growth factors, other growth factors may be added to the culture medium that influence proliferation and differentiation of the cells including NGF, platelet-derived growth factor (PDGF), thyrotropin releasing hormone (TRH), transforming growth factor betas (TGFβs), insulin-like growth factor (IGF-1) and the like.

Conditions for culturing should be close to physiological conditions. The pH of the culture medium should be close to physiological pH, preferably between pH 6-8, more preferably between about pH 7 to 7.8, with pH 7.4 being most preferred. Physiological temperatures range between about 30° C. to 40° C. Cells are preferably cultured at temperatures between about 32° C. to about 38° C., and more preferably between about 35° C. to about 37° C.

Determining the Effect of an Agent on Tissue Stem Cell Kinetics (Tissue Stem Cells, Transient Cells and Differentiated Cells)

Methods are provided that allow for determination of the effect of an agent on a heterogeneous population of cells comprising tissue stem cells, transient cells and terminally differentiated cells. The methods comprises culturing the heterogeneous population of cells comprising tissue stem cells, transient cells and terminally differentiated cells, as described above, herein, and contacting the cultured cells with an agent. Sequential passages of the cultured cells are then preformed based on a specific time interval for passage rather than passage based on cell density, wherein the cells are sequentially passaged at the specific time interval using the same dilution factor at each passage such that the cells do not reach more than 50% confluency at the time for passage until at least two passages are performed without any increase in cell number in the culture prior to next passage.

At the time of each passage the number of cells in the heterogeneous population is determined so that the number of population doubling versus time of passage can be plotted to obtain a growth curve for the heterogeneous population. The growth curve is then compared to the growth curve of a control isogenic culture that has not been contacted with the test agent. A deviation of the growth curve in the presence of the test agent from the control growth curve indicates the agent has either a toxic or a positive effect on tissue stem cells, transient cells, or terminal cells.

An agent can positively affect tissue stem cells or transient cells if there is an increase in tissue stem/transient cell number, viability, or function. While an agent that affects a decrease in cell number, viability, or function, of tissue stem cells, transient cell, or terminal cells, is said to have a toxic effect.

In an alternative embodiment, rather than passaging the cells until at least two passages result in no increase in cell number, the cells are passaged until the culture has less than 40%, 30%, 20%, or 10% of the cell number initially plated within 100 days, within 90 days or within 80 days of sequential passage.

As used herein, the term "contacting" or "contact" in connection with contacting the heterogeneous cell population (e.g. freshly isolated cells or cultured cells) with a test agent, includes subjecting the cells to a culture media, which comprises the compound (test agent). In certain embodiments, the contacting can occur prior to isolation of the cells from the subject, or tissue, e.g. by administration of an agent to a subject. Though a benefit of the present invention is that it can serve as a purely in vitro method. In some embodiments, the contacting with the agent is only done prior to the sequential passaging. In one embodiment, the agent is provided to media throughout the growth curve analysis, e.g. at every sequential passage. In some embodiments, at least two passages, or at least three, or at least four passages and so on. Those of skill in the art can vary the time period for contacting the cells and/or the concentration of the agent in order to obtain a suitable growth curve for analysis.

Any test agent can be used in methods of the invention. As used herein, the terms "test compound" or "test agent" are used interchangeably and refers to compounds and/or compositions that are to be tested for their ability to stimulate growth or viability of tissue stem cells, transient cells etc., or to identify agents that are toxic to such cells. The test agents can include a wide variety of different compounds, including known drugs and unknown drugs, including chemical compounds and mixtures of chemical compounds, e.g., small molecules, e.g. small organic or inorganic molecules; saccharines; oligosaccharides; polysaccharides; biological macromolecules, e.g., peptides, proteins, and peptide analogs and derivatives; peptidomimetics; nucleic acids; antibodies, nucleic acid analogs and derivatives; an extract made from biological materials such as bacteria, plants, fungi, or animal cells; animal tissues; naturally occurring or synthetic compositions; and any combinations thereof.

As used herein, the term "small molecule" refers to in organic or organic compounds. However, small molecules typically are characterized in that they contain several carbon-carbon bonds, and have a molecular weight of less than 5000 Daltons (5 kD), preferably less than 3 kD, still more preferably less than 2 kD, and most preferably less than 1 kD.

The number of possible test agents runs into millions. Of particular interest are compounds that have been deemed useful for the treatment of a disease in in vitro studies or in in vivo studies, e.g. therapeutic compounds. In certain embodiments, the compounds can be screened in vitro before animal model testing is even attempted thereby reducing failures at the stage of animal testing for the therapeutic agent. In addition, using the methods described herein, a compound library can be compiled of all compounds that show either an increase in growth and viability of tissue stem cells (and/or transient cells), or that are neutral to tissue stem cells and transient cells, that can be used as test agents in therapeutic screens.

All therapeutic compounds are of interest, and include, but are not limited to, agents for treatment of cancer, viral infections, bacterial infections, fungus infections, heart disease, liver disease, cardiovascular disease, obesity, for facilitation of wound healing, for treatment of pain, allergies, inflammation, for treatment of genetic disorders (e.g. hemophilia, cystic fibrosis, neurodegeneration), for treatment of diabetes, high blood pressure, and the like.

An agent can be a nucleic acid RNA or DNA, and can be either single or double stranded. Example nucleic acid compounds include, but are not limited to, a nucleic acid encoding a protein activator or inhibitor (e.g. transcriptional activators or inhibitors), oligonucleotides, nucleic acid analogues (e.g. peptide-nucleic acid (PNA), pseudo-complementary PNA (pc-PNA), locked nucleic acid (LNA) etc.), antisense molecules, ribozymes, small inhibitory or activating nucleic acid sequences (e.g. RNAi, shRNA, siRNA, micro RNAi (mRNAi), antisense oligonucleotides etc.) A protein and/or peptide agent can be any protein that modulates gene expression or protein activity. Non-limiting examples include mutated proteins; therapeutic proteins and truncated proteins. Proteins can also be selected from genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof.

Test agents can be small molecule compounds, e.g. methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule, Pharmacopia, graffinity, Panvera, Vitas-M Lab, Biomol International and Oxford. These libraries can be screened using the screening devices and methods described herein. Chemical compound libraries such as those from NIH Roadmap, Molecular Libraries Screening Centers Network (MLSCN) can also be used.

Generally, agents can be tested at any concentration that can modulate growth relative to a control over an appropriate time period. Typically a range of concentrations is tested for any given agent. In some embodiments, compounds are tested at concentration in the range of about 0.1 nM to about 1000 mM. In one embodiment, the compound is tested in the range of about 0.1 $\mu$M to about 20 $\mu$M, about 0.1 $\mu$M to about 10 $\mu$M, or about 0.1 $\mu$M to about 5 $\mu$M. In one embodiment, compounds are tested at 1 $\mu$M.

In certain embodiments, a toxicity profile is obtained by testing a range of concentrations on isogenic populations of cells and plotting the data to determine the LD50 (the dose lethal to 50% of the population) and/or the ED50 (the dose positively effective in 50% of the population). The dose ratio between toxic and therapeutic effects is the therapeutic index and it can be expressed as the ratio LD50/ED50. Compositions that exhibit large therapeutic indices are preferred.

When determining the effect by the methods described herein, it may be desirable to use a positive control, for example a drug whose effect on tissue stem cell kinetics (FIG. 1) is already known. Table 1 provides just an example of such drugs, there are many drugs known to those of skill in the art that have an effect on tissue stem cell kinetics.

TABLE I

Example positive control agents

| Agent | Cell-type Specificity | Clinical Effects |
|---|---|---|
| [PBS] | None | Control condition |
| xanthosine | SC[a] | (In vitro, increases tissue SC self-replication)[1-5] |
| ponatinib | SC | Inclusig ®; myelosuppressive |
| idarubicin | SC | Targets hematopoietic progenitors |
| tipifarnib | SC | Highly toxic with myelosuppression |
| imatinib mesylate | TC[b] | Gleevac ®; minimal cytotoxic effects |
| cyclophosphamide | SC and TC | Cytoxan ®; extremely myelosuppressive |
| refecoxib | SC and TC | Vioxx ®; idiosyncratic life-threatening toxicity |

[a]SC, tissue stem cells;
[b]TC, transient cells

Depending upon the particular embodiment being practiced, the test agents can be provided free in solution, or may be attached to a carrier, or a solid support.

In certain embodiments, the test agents are combined, formulated with a "pharmaceutically acceptable carrier." As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation.

The amount of agent that is combined with a carrier material to produce a single dosage form will generally be that amount of the compound that produces a therapeutic effect. Generally out of one hundred percent, this amount will range from about 0.1% to 99% of compound, preferably from about 5% to about 70%, most preferably from 10% to about 30% of the composition.

When one observes a deviation in the kinetic growth curve in the presence of the test agent then an effect of the agent is indicated, either a positive or a toxic effect. By analyzing where the deviation occurs within the curve one can discern if the effect of the agent is on tissue stem cells, transient cells, or terminally differentiated cells. Example deviations between the growth curves in the presence and absence of a test agent that can be observed are described in the Example 2. For example, when the deviation of the curve is due to a lower amount population doublings early in the growth curve and to a faster time to reach the two passages that are performed without any increase in cell number (See e.g. FIG. 7), the agent is toxic to tissue stem cells. However, when the deviation of the curve is due to a lower amount population doublings late in the growth curve, and the time to reach the two passages that are performed without any increase in cell number in the culture prior to next passage (See e.g. FIG. 9) is similar to the control, the agent is toxic to transient cells. In addition, when the deviation of the curve is due to a higher amount of population doublings in the middle of the growth curve, and the time to reach the two passages are performed without any increase in cell number (is similar to the control, the agent has a positive effect on tissue stem cells (See e.g. FIG. 12). Deviations in the curves can also differentiate between toxicity to terminal or transient cells (See FIG. 11), or when an agent is toxic to both transient and stem cells (See FIG. 10).

To determine what is early in the growth phase, late in the growth phase, and what is in the middle of the growth phase, the skilled artisan divides the total days in the growth curve into three equal parts, a first "early phase", a second "middle phase", and a third "late phase." For example, an 87 day curve is split into three phases of 29 days; within day 1-29 early phase, within day 30-58 middle phase, and within day 59-87 late phase.

Unless otherwise explained, all technical and scientific terms used herein have the same meaning as commonly understood by one of ordinary skill in the art to which this disclosure belongs.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The terms "enriching" or "enriched" are used interchangeably herein and mean that the yield (fraction) of cells of one type is increased by at least 10% over the fraction of cells of that type in the starting culture or preparation.

In certain embodiments, analysis of the data obtained from the methods described herein is implemented by computer systems. Accordingly, also provided are computer readable mediums and computer systems comprising data modules, storage modules, and comparison modules, that enable plotting of the growth curves, and enable the comparison of growth curves treated and not treated with agent. The various derivations of the curve can then signal through a signaling module, if and how the test agent is toxic to cells.

In one embodiment, when the deviation of the curve is due to a lower amount of population doublings early in the growth curve and to a faster time to reach the two passages that are performed without any increase in cell number, the signaling module will signal the agent is toxic to tissue stem cells.

In one embodiment, when the deviation of the curve is due to a lower amount of population doublings late in the growth curve, and the time to reach the two passages that are performed without any increase in cell number in the culture is similar to the control, the signaling module will signal the agent is toxic to transient cells.

In one embodiment, when the deviation of the curve is due to a higher amount of population doublings in the middle of the growth curve, and the time to reach the least two passages that are performed without any increase in cell is similar to the control, the signaling module will signal the agent has a positive effect on tissue stem cells.

In one embodiment, the signaling module will signal a positive effect that is due to an increase in tissue stem cell number, viability, or function.

In one embodiment, the signaling module will signal a toxic effect that is due to a decrease in tissue stem cell number, viability, or function.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Unless otherwise stated, the present invention was performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Methods in Enzymology: Guide to Molecular Cloning Techniques Vol. 152, S. L. Berger and A. R. Kimmerl Eds., Academic Press Inc., San Diego, USA (1987)); Current Protocols in Molecular Biology (CPMB) (Fred M. Ausubel, et al. ed., John Wiley and Sons, Inc.); Current Protocols in Cell Biology (CPCB) (Juan S. Bonifacino et. al. ed., John Wiley and Sons, Inc.); Culture of Animal Cells: A Manual of Basic Technique by R. Ian Freshney, Publisher: Wiley-Liss; 5th edition (2005); and Animal Cell Culture Methods (Methods in Cell Biology, Vol. 57, Jennie P. Mather and David Barnes editors, Academic Press, 1st edition, 1998) which are all incorporated by reference herein in their entirety.

Other than in the operating examples, or where otherwise indicated, all numbers expressing quantities of ingredients or media conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

In some embodiments of the present invention may be defined in any of the following numbered paragraphs:

Paragraph 1. An in vitro method of culturing a heterogeneous population of cells that allows for determination of the effect of an agent on the tissue stem cells comprising: a) culturing a heterogeneous population of cells comprising tissue stem cells, transient cells and terminally differentiated cells; and b) performing sequential passages of the cultured cells of step a) based on a specific time interval for passage rather than passage based on cell density, wherein the cells are sequentially passaged at the specific time interval using the same dilution factor at each passage such that the cells do not reach more than 50% confluency at the time for passage, and wherein the cells are sequentially passaged until at least two passages are performed without any increase in cell number in the culture prior to next passage; thereby allowing the number and cell kinetics of tissue stem cells, transient cells and terminally differentiated cells within the population to be monitored.

Paragraph 2. The method of paragraph 1, wherein there is a decline in the cell number of the culture at the time of passage, as compared to the cell number at the time of a prior passage, within 6 sequential passages.

Paragraph 3. The method of paragraph 1, wherein the period of time until at least two passages are performed without any increase in cell number in the culture is less than 100 days.

Paragraph 4. The method of paragraph 1, wherein the period of time until at least two passages are performed without any increase in cell number in the culture is less than 90 days.

Paragraph 5. The method of paragraph 1, wherein the period of time until at least two passages are performed without any increase in cell number in the culture is less than 80 days.

Paragraph 6. The method of paragraph 1, wherein less than 50,000 cells/cm$^2$ are cultured in step a).

Paragraph 7. The method of paragraph 1, wherein less than 10,000 cells/cm$^2$ are cultured in step a).

Paragraph 8. The method of paragraph 1, wherein less than 7,000 cells/cm$^2$ are cultured in step a).

Paragraph 9. The method of paragraph 1, wherein the specific time interval is every 108 hours.

Paragraph 10. The method of paragraph 1, wherein the specific time interval is every 96 hours.

Paragraph 11. The method of paragraph 1, wherein the specific time interval is every 72 hours.

Paragraph 12. The method of paragraph 1, wherein the specific time interval is every 48 hours.

Paragraph 13. The method of paragraph 1, wherein the dilution factor is 1:2.

Paragraph 14. The method of paragraph 1, wherein the dilution factor is 1:3.

Paragraph 15. The method of paragraph 1, wherein the dilution factor is 1:5.

Paragraph 16. The method of paragraph 1, wherein the dilution factor is 1:10.

Paragraph 17. The method of paragraph 1, wherein the cell number at the two passages that are performed without any increase in cell number has declined to less than 40% of the cell number in step a).

Paragraph 18. The method of paragraph 1, wherein the cell number at the two passages that are performed without any increase in cell number has declined to less than 30% of the cell number in step a).

Paragraph 19. The method of paragraph 1, wherein the cell number at the two passages that are performed without any increase in cell number has declined to less than 20% of the cell number in step a).

Paragraph 20. The method of paragraph 1, wherein the cell number at the two passages that are performed without any increase in cell number has declined to less than 10% of the cell number in step a).

Paragraph 21. The method paragraph 1, wherein the percentage of tissue stem cells in the population is less than 5%.

Paragraph 22. An in vitro method of determining the effect of an agent on a heterogeneous population of cells comprising tissue stem cells, transient cells and terminally differentiated cells, comprising: a) culturing a heterogeneous population of cells comprising tissue stem cells, transient cells and terminally differentiated cells, b) contacting the cultured cells of step a) with an agent; c) performing sequential passages of the cultured cells of step b) based on a specific time interval for passage rather than passage based on cell density, wherein the cells are sequentially passaged at the specific time interval using the same dilution factor at each passage such that the cells do not reach more than 50% confluency at the time for passage, and wherein the cells are sequentially passaged until at least two passages are performed without any increase in cell number in the culture prior to next passage; d) determine the number of cells in the heterogeneous population at the time of each passage; e) plotting the number of population doubling versus time of passage to obtain a growth curve for the heterogeneous population; and f) comparing the growth curve of step e) to a control culture that has not been contacted with the agent of step b), wherein a deviation of the curve of step e) from the control indicates the agent has either a toxic or a positive effect on tissue stem cells, transient cells, or terminal cells.

Paragraph 23. The method of paragraph 22, wherein when the deviation of the curve is due to a lower amount of population doublings early in the growth curve and to a faster time to reach the two passages that are performed without any increase in cell number, the agent is toxic to tissue stem cells.

Paragraph 24. The method of paragraph 22, wherein when the deviation of the curve is due to a lower amount of population doublings late in the growth curve, and the time to reach the two passages that are performed without any increase in cell number in the culture is similar to the control, the agent is toxic to transient cells.

Paragraph 25. The method of paragraph 22, wherein when the deviation of the curve is due to a higher amount of population doublings in the middle of the growth curve, and the time to reach the least two passages that are performed without any increase in cell is similar to the control, the agent has a positive effect on tissue stem cells.

Paragraph 26. The method of paragraph 22, wherein the positive effect is an increase in tissue stem cell number, viability, or function.

Paragraph 27. The method of paragraph 22, wherein the toxic effect is a decrease in tissue stem cell number, viability, or function.

Paragraph 28. The method of paragraph 22, wherein there is a decline in the cell number of the culture at the time of passage, as compared to the cell number at the time of a prior passage, with six sequential passages.

Paragraph 29. The method of paragraph 22, wherein the period of time until at least two passages are performed without any increase in cell number in the culture is less than 100 days.

Paragraph 30. The method of paragraph 22, wherein the period of time until at least two passages are performed without any increase in cell number in the culture is less than 90 days.

Paragraph 31. The method of paragraph 22, wherein the period of time until at least two passages are performed without any increase in cell number in the culture is less than 80 days.

Paragraph 32. The method of paragraph 22, wherein less than 50,000 cells/cm$^2$ are cultured in step a).

Paragraph 33. The method of paragraph 22, wherein less than 10,000 cells/cm$^2$ are cultured in step a).

Paragraph 34. The method of paragraph 22, wherein less than 7,000 cells/cm$^2$ are cultured in step a).

Paragraph 35. The method of paragraph 22, wherein the specific time interval is every 108 hours.

Paragraph 36. The method of paragraph 22, wherein the specific time interval is every 96 hours.

Paragraph 37. The method of paragraph 22, wherein the specific time interval is every 72 hours.

Paragraph 38. The method of paragraph 22, wherein the specific time interval is every 48 hours.

Paragraph 39. The method of paragraph 22, wherein the dilution factor is 1:2.

Paragraph 40. The method of paragraph 22, wherein the dilution factor is 1:3.

Paragraph 41. The method of paragraph 22, wherein the dilution factor is 1:5.

Paragraph 42. The method of paragraph 22, wherein the dilution factor is 1:10.

Paragraph 43. The method paragraph 22, wherein the percentage of tissue stem cells in the population is less than 5%.

Paragraph 44. The method of paragraph 22, wherein the cell number at the two passages that are performed without any increase in cell number has declined to less than 40% of the cell number in step a).

Paragraph 45. The method of paragraph 22, wherein the cell number at the two passages that are performed without any increase in cell number has declined to less than 30% of the cell number in step a).

Paragraph 46. The method of paragraph 22, wherein the cell number at the two passages that are performed without any increase in cell number has declined to less than 20% of the cell number in step a).

Paragraph 47. The method of paragraph 22, wherein the cell number at the two passages that are performed without any increase in cell number has declined to less than 10% of the cell number in step a).

Paragraph 48. An in vitro method of culturing a heterogeneous population of cells that allows for determination of the effect of an agent on the tissue stem cells within the heterogeneous population comprising: performing sequential passaging of a heterogeneous population of cells comprising tissue stem cells, transient cells, and terminally differentiated cells, in a manner that the cells in culture cease to divide within a period of 100 days (within 90, 80, 60, days), thereby allowing the number and cell kinetics of tissue stem cells, transient cells and terminally differentiated cells to be monitored within the population.

EXAMPLES

Example 1: An Example Passage Schedule for the Invention

What follows is an example of serial culturing schedule that embodies the principles of the invention. The starting cell number, vessel size, dilution amount, and dilution interval may be varied to achieve efficiencies of time and scale. However, strict adherence to the time interval fixed dilution schedule such that the cells never reach more than 50% confluency at the time of any passage in the sequence so that a decline in cell number is observed (e.g. to less than 50%, 40%, 30%, 20%, or 10% of original cell number) in a period of time until at least two intervals have occurred without increase in cell number are important requirements. For example in a period of time less than 100 days, (e.g. less than 90 days, or less than 80 days). The decline in cell number occurs faster than one would observe in cell cultures of primary cells that are passaged using a schedule based on cell number, which is typically corresponds to ≤50 cumulative population doublings resulting in about 150-200 days of culture before they stop dividing. The less dense population of cells (i.e. so the peak cell number at the time of passage results in never greater than 50% confluency) results in a cell culture that rapidly declines in cell number, as compared to recommended cell culture passaging schedules for primary cells, because the cells are not densely populated and for optimal cell growth the cells like to be close to one another.

1. Set-up all 6 wells of a six-well plate with 65,000 viable cells in each well with 5 mLs total medium in each well.

2. Culture for 96 Hours.

3. At the end of the 96-hour culture interval, each well should be trypsinized, respectively, and ⅓ of its cells transferred (within a 1 mL volume of culture medium) to a respective well of a new 6-well plate with 5 mLs of culture medium. Each 6-well culture's passaging is consistently maintained respectively, distinct of others. (If a suspension culture is being used, cells are simply removed for counting and dilution.)

4. The remaining ⅔ cells are used for counting as soon as the new plates are completed and returned to the incubator. Minimize the amount of time that the transferred cells are in non-ideal conditions. Thereafter, the cell counts should be conducted immediately to minimize loss of viability due to non-ideal conditions. Do not put the cells for counting on ice or chill. Generally, a coefficient of variation ≤5% is required for individual well counts. Both viable and total counts should be determined.

5. The new cultures are grown for 96 hours and the ⅓ dilution-counting procedure repeated.

6. This "culture 96 hours, ⅓ dilution, count" procedure should be continued until two successive passages result in no increase in cell number.

The culture schedule described herein is distinct from the conventional manner in which primary human cell cultures have been maintained previously. All primary human tissue cultures contain the three main cell kinetics categories of tissue cells, as illustrated in FIG. 1, which include rare tissue stem cells, abundant transient amplifying cells (which also include lineage-committed progenitor cells), and abundant terminally differentiated cells.

Figure 2:
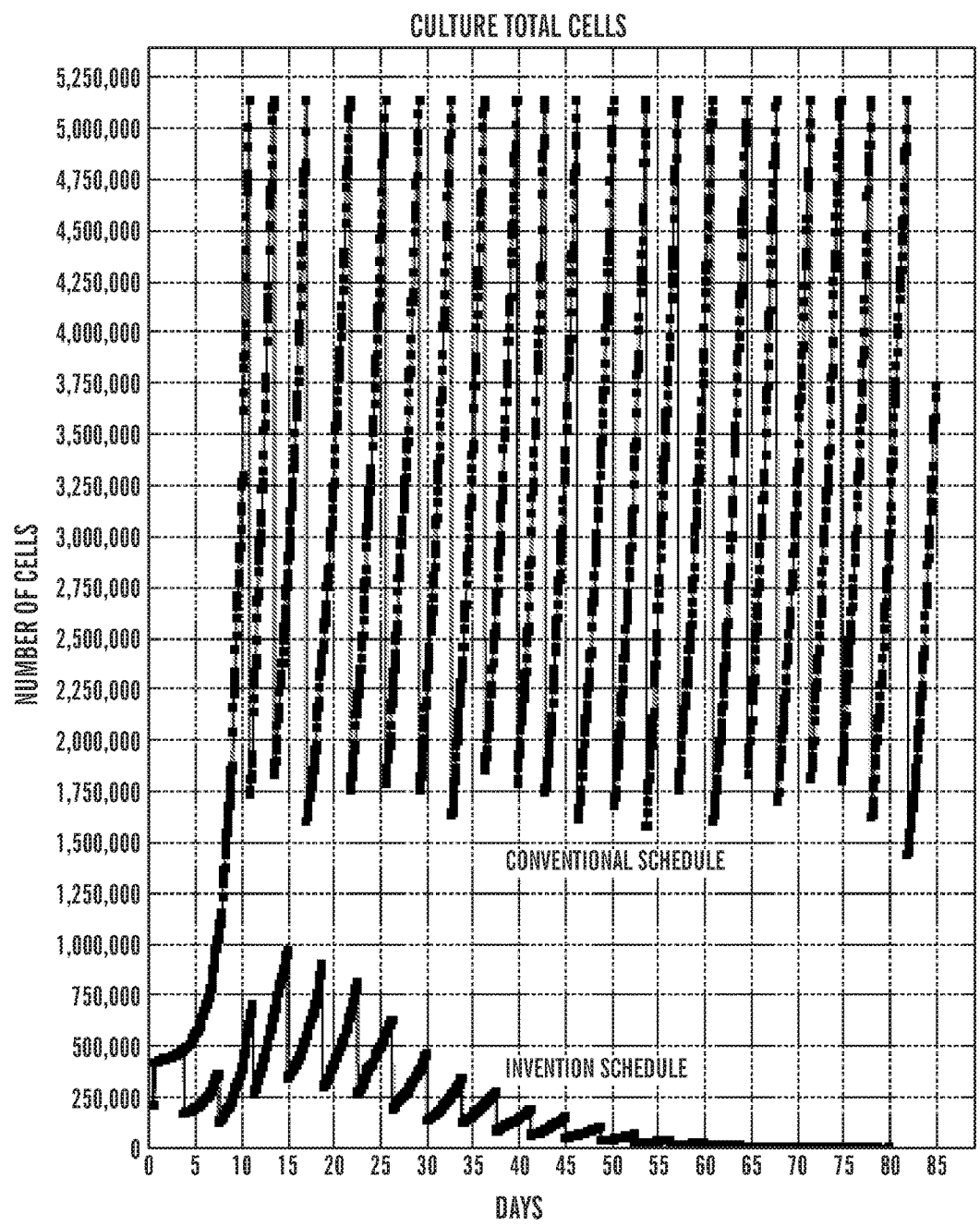
FIG. 2 shows a graph of one embodiment of computer-simulation of total cell number with culture transfers on the invention schedule and the conventional schedule employed for human cells. Simulation was stopped at 85 days. Note how the conventional schedule depends on culture confluency (i.e., reaching the culture vessel's maximum cell capacity before each dilution).

Computer-simulation can be used to illustrate the significant differences in the conventional human cell culture schedule and the invention. FIG. 2 shows a comparison of the progression of total cell number for cell cultures that only differ for their culture schedule. The output of the invention schedule is compared to that of the conventional schedule for human tissue cells. In the conventional schedule for human cells, investigators wait until cultures reach confluency (~5 million cells in the simulation for a 75-cm2 flask) before transferring a fixed fraction of the cells (8). In another schedule used for rodent cells, a number of cells equivalent to the starting number is transferred at a fixed interval (9). Therefore, the transfer fraction varies. The invention schedule differs from both by dictating that a fixed fraction of the cells is transferred at a fixed interval, no matter how many cells are present at the end of each growth interval.

As result of this distinction, conventional cultures continue to grow for a longer period (>85 days in the simulation) than cultures on the invention schedule (≤85 days in the simulation), which is designed to effect a more rapid dilution of tissue stem cells.

Figure 3:
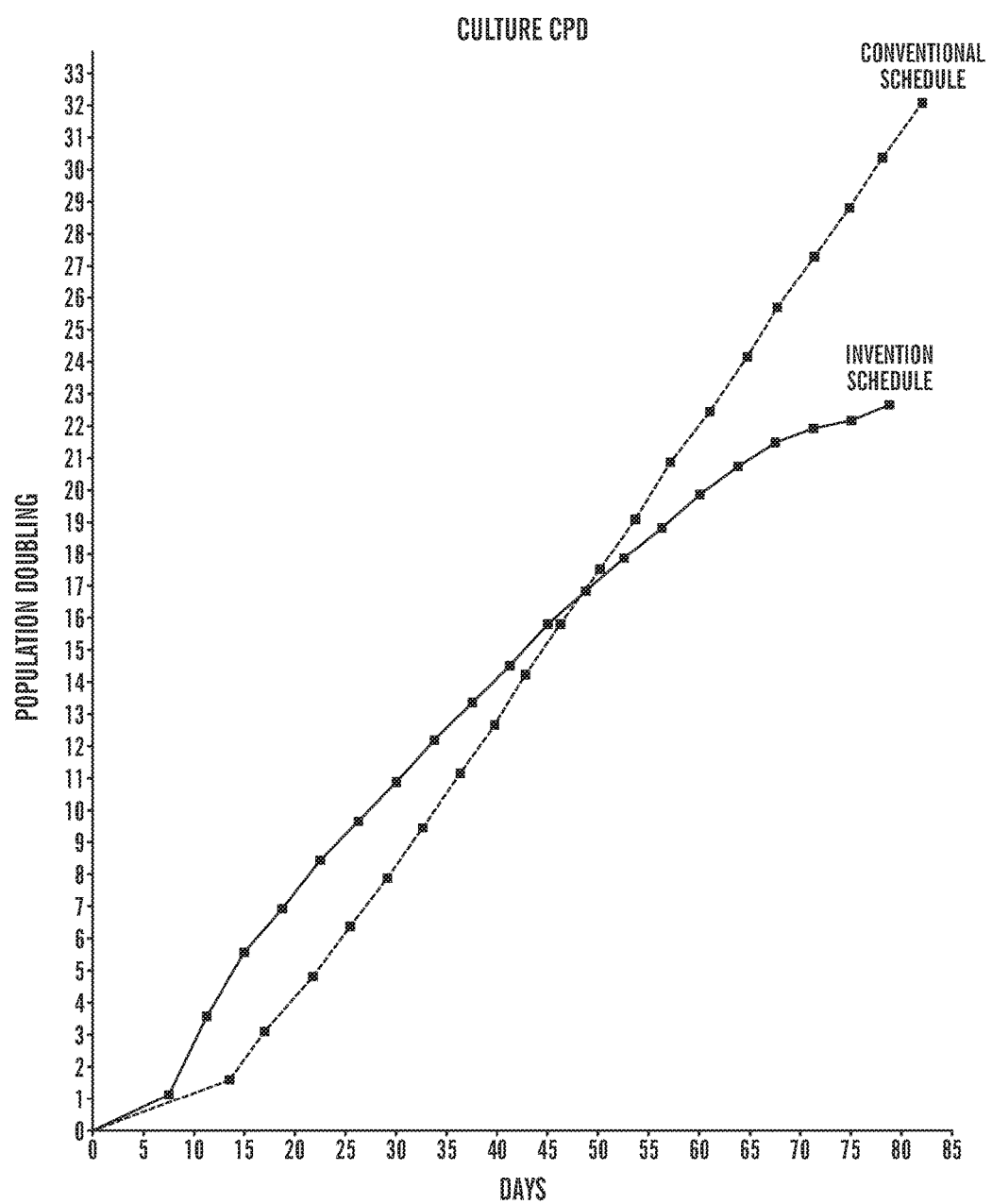
FIG. 3 shows a graph of the corresponding cumulative population doublings (CPD) output for human liver tissue cells cultured on one embodiment of the invention schedule compared to culture on the conventional schedule (based on FIG. 2 analyses).
Figure 4:
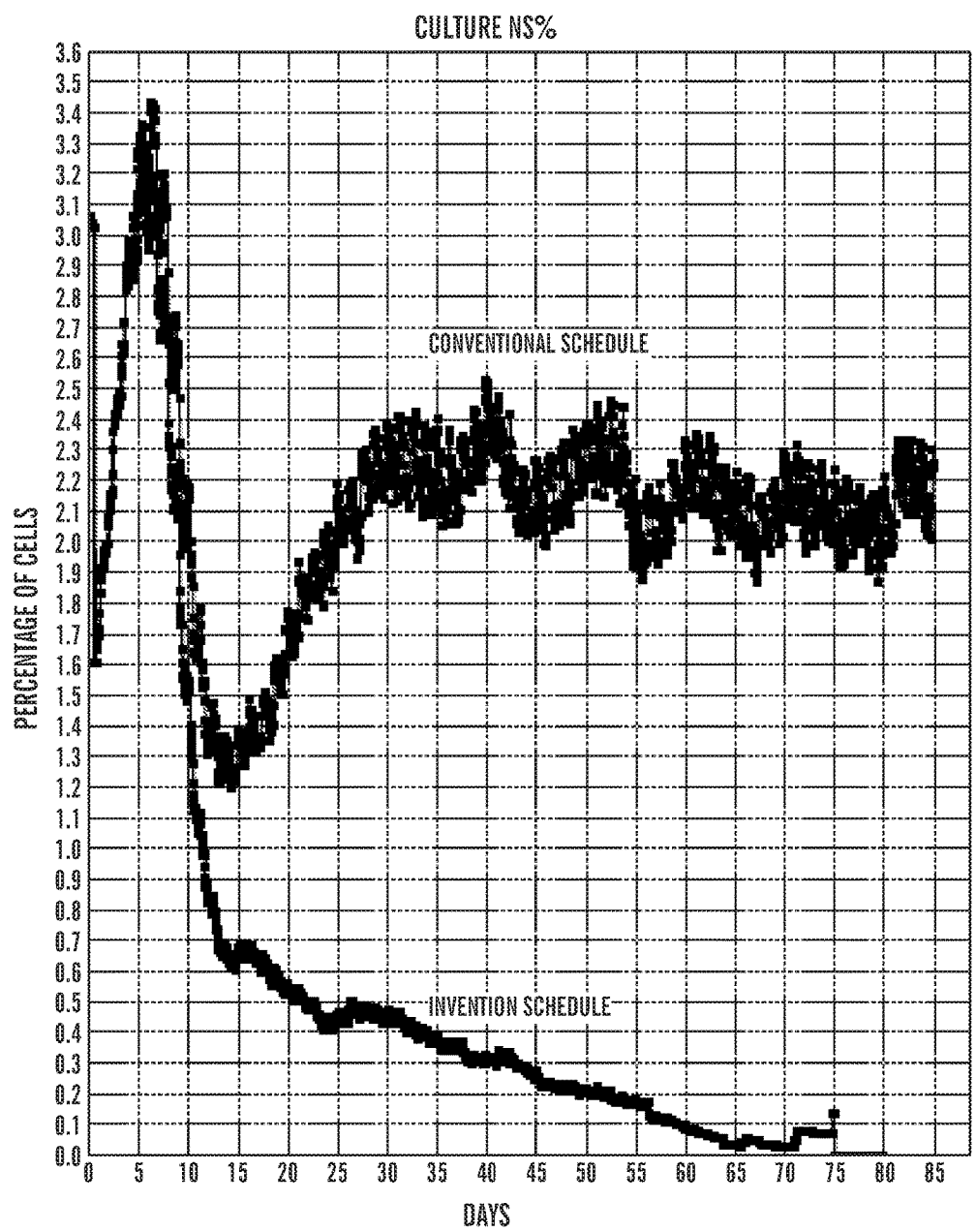
FIG. 4 shows a graph of a computer-simulation to illustrate the differences in the rate of tissue stem cell dilution for the invention schedule versus the conventional schedule. Note how the conventional schedule results in stabilization of tissue stem cell fraction, which precludes the statistical deviation required to distinguish cell type-specific effects.

FIG. 3 shows how this difference in culture schedule is reflected in distinct population doubling outputs, including the continued growth of the conventional culture (for as many as 150 days). The computer-simulation in FIG. 4 shows how the difference in culture growth is related to differences in the rate of tissue stem cell dilution, which underpins the ability of the invention to distinguish the cell type-specificity of toxic or activating agents.

Example 2: Determination of the Cell Type Specificity of Agents

Computer-simulation can be employed to demonstrate that the invention schedule can be used to determine if any, and which, of the three different cell kinetics types of tissue cells are killed by a test agent.

Figure 5:
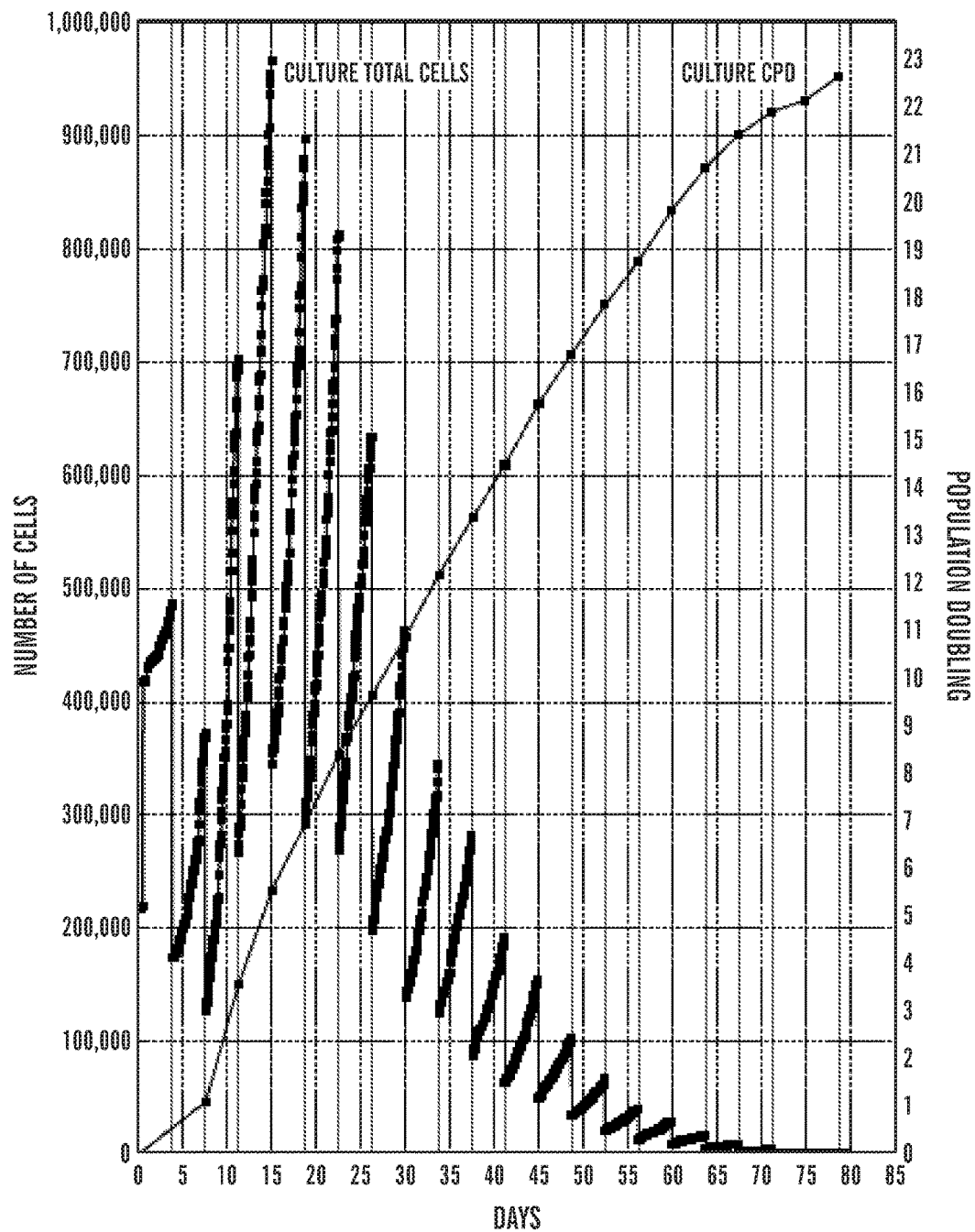
FIG. 5 shows a graph of a computer-simulation of the total cell number output produced by serial culture of human liver cells. These data are transformed into cumulative population doubling data for cell kinetics analyses (culture CPD). Vertical lines denote culture dilution events.

FIG. 5 shows a computer-simulation of a primary human liver cell culture estimated to have an initial stem cell fraction of 0.035 (10). Investigators are able to determine the peak cell number of the serial culture before each ⅓ dilution, which occurs every 96 hours (equally-spaced vertical lines). These values are used to calculate the cumulative population doubling kinetics used for culture comparisons.

Figure 6:
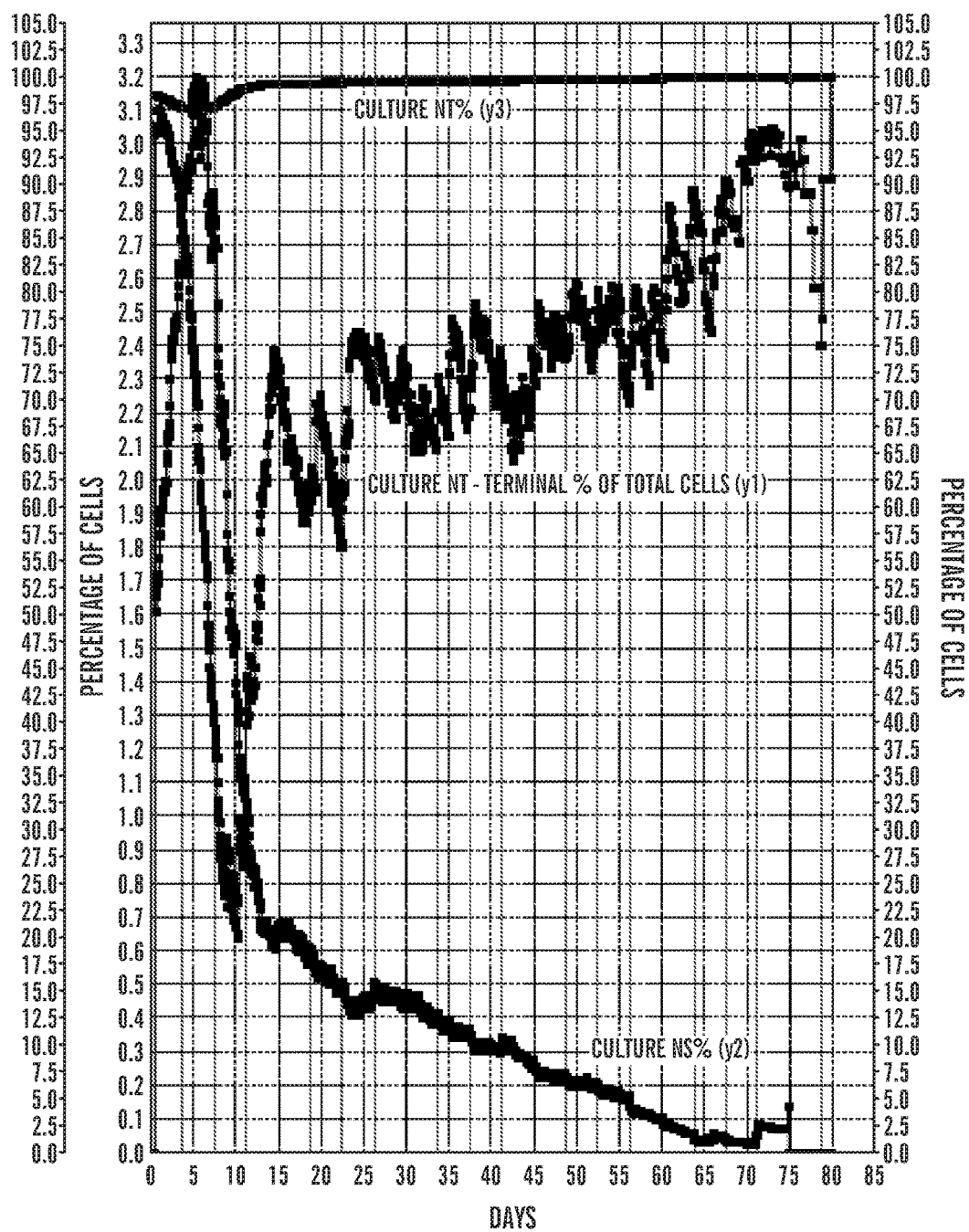
FIG. 6 shows a graph of a computer-simulated deconstruction of the stem cell, transient cell, and terminal cell components of the total cell data in FIG. 2.

FIG. 6 shows a computer-simulated deconstruction of the total cell number data into component percentages of tissue stem cells (NS %), transient cells (NT %), and terminal cells (NT-Terminal %). After an initial increase in their percentage, tissue stem cells are loss from culture altogether by systematic cell kinetics dilution. The terminal cell fraction initially equilibrates to approximately half of the total cells present, as dictated by the universal tissue cell hierarchy. However, soon after the loss of all tissue stem cells, all the remaining cells in the culture progress to terminal cells. This progression is due to the absence of tissue stem cells that are required for the production of transient cells, which are the precursors for terminal cells.

Figure 7:
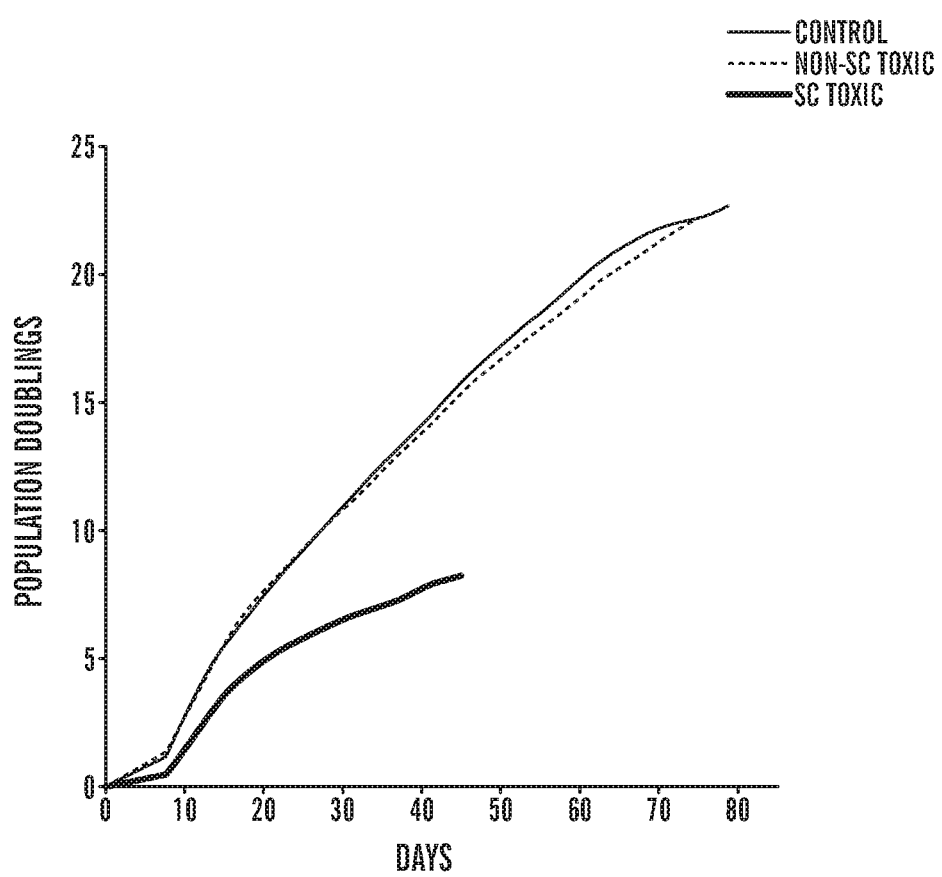
FIG. 7 shows a graph of a comparison of computer-simulated cell kinetics data for control serial culture, serial culture with a non-stem cell toxic agent at its IC50, and serial culture with a stem cell toxic agent at its IC50.
Figure 8:
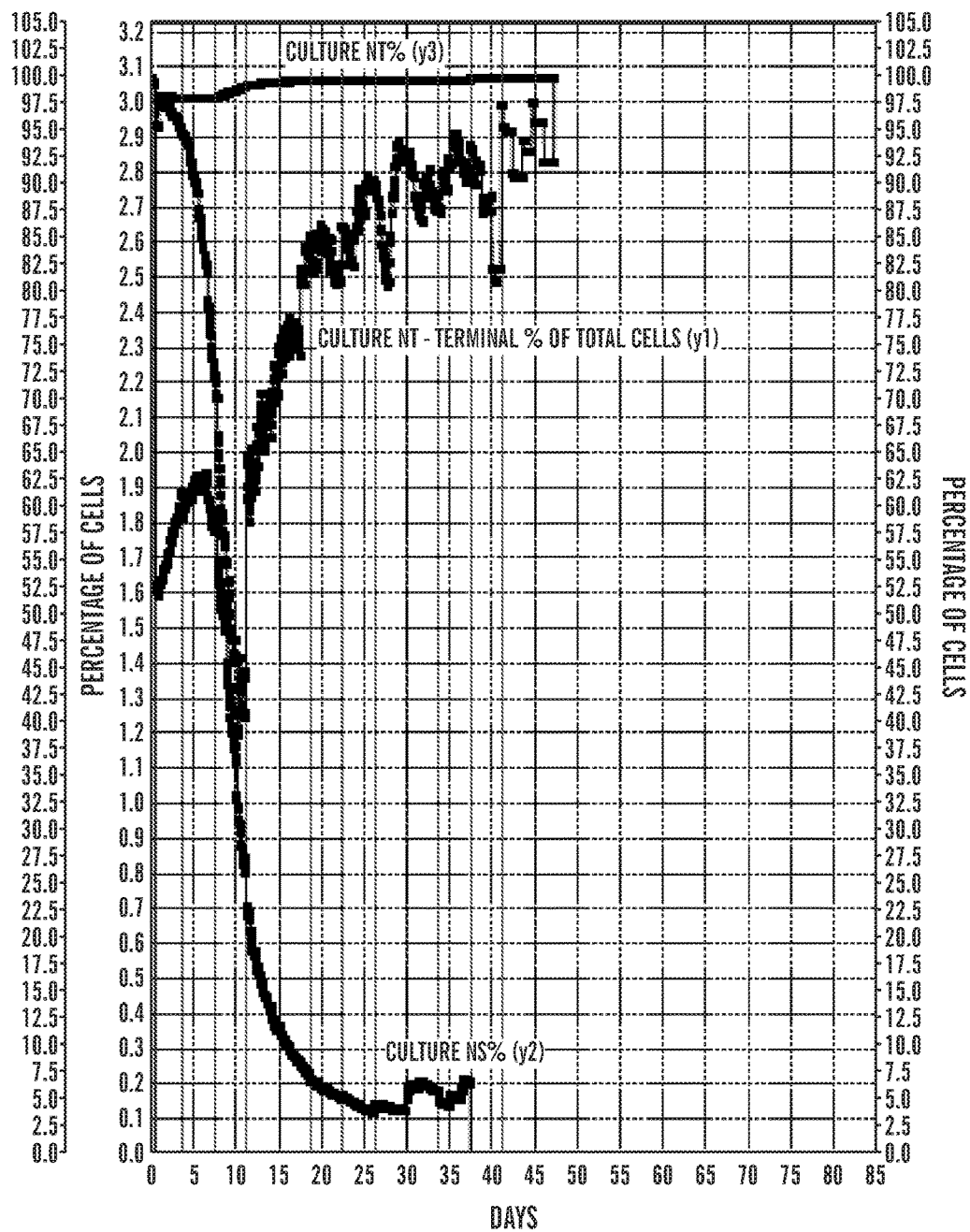
FIG. 8 shows a graph of a computer-simulated deconstruction of the stem cell, transient cell, and terminal cell components of the cell kinetics data in FIG. 7 for serial culture with a stem cell toxic agent.

FIG. 7 compares the effects of two different classes of drugs on serial culture cell kinetics. At its IC50 (concentration that gives 50% inhibition), a drug that causes the death of transient cells and terminal cells causes a detectable and characteristic, but modest, change in the culture cell kinetics (dotted line). In contrast, a stem cell toxic drug, also at its IC50, induces profound qualitative and quantitative changes in the cell kinetics output. FIG. 8 provides a computer-simulated deconstruction to show the specific effect of the stem cell toxic drug to reduce stem cell number, which accelerates tissue stem cell dilution.

Figure 9:
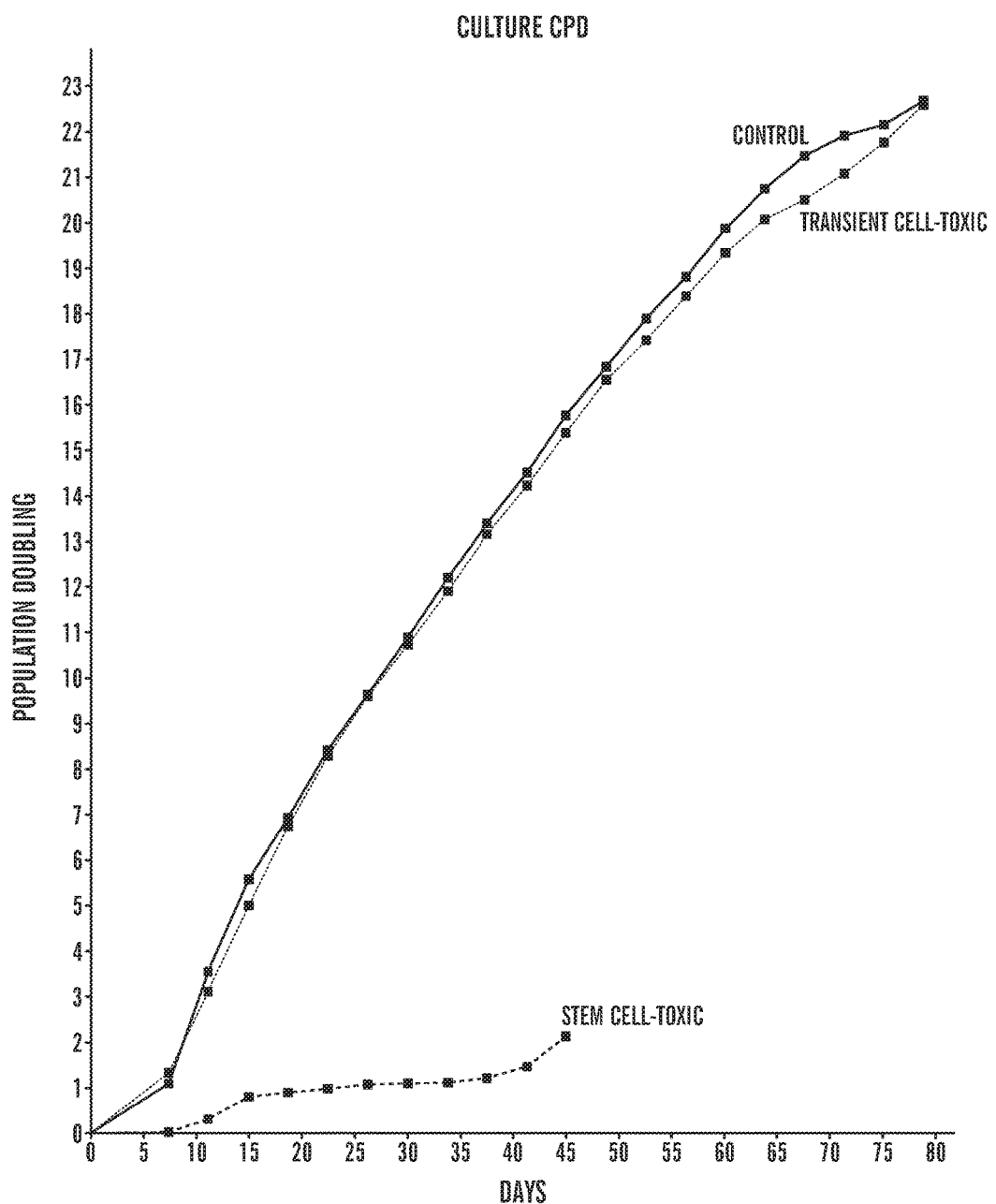
FIG. 9 shows a graph of a comparison of computer-simulated cell kinetics data for an untreated control serial culture, a serial culture treated with a transient cell-specific toxic agent at its IC90, and a serial culture treated with a tissue stem cell-specific toxic agent at its IC90. CDP, cumulative population doublings.
Figure 10:
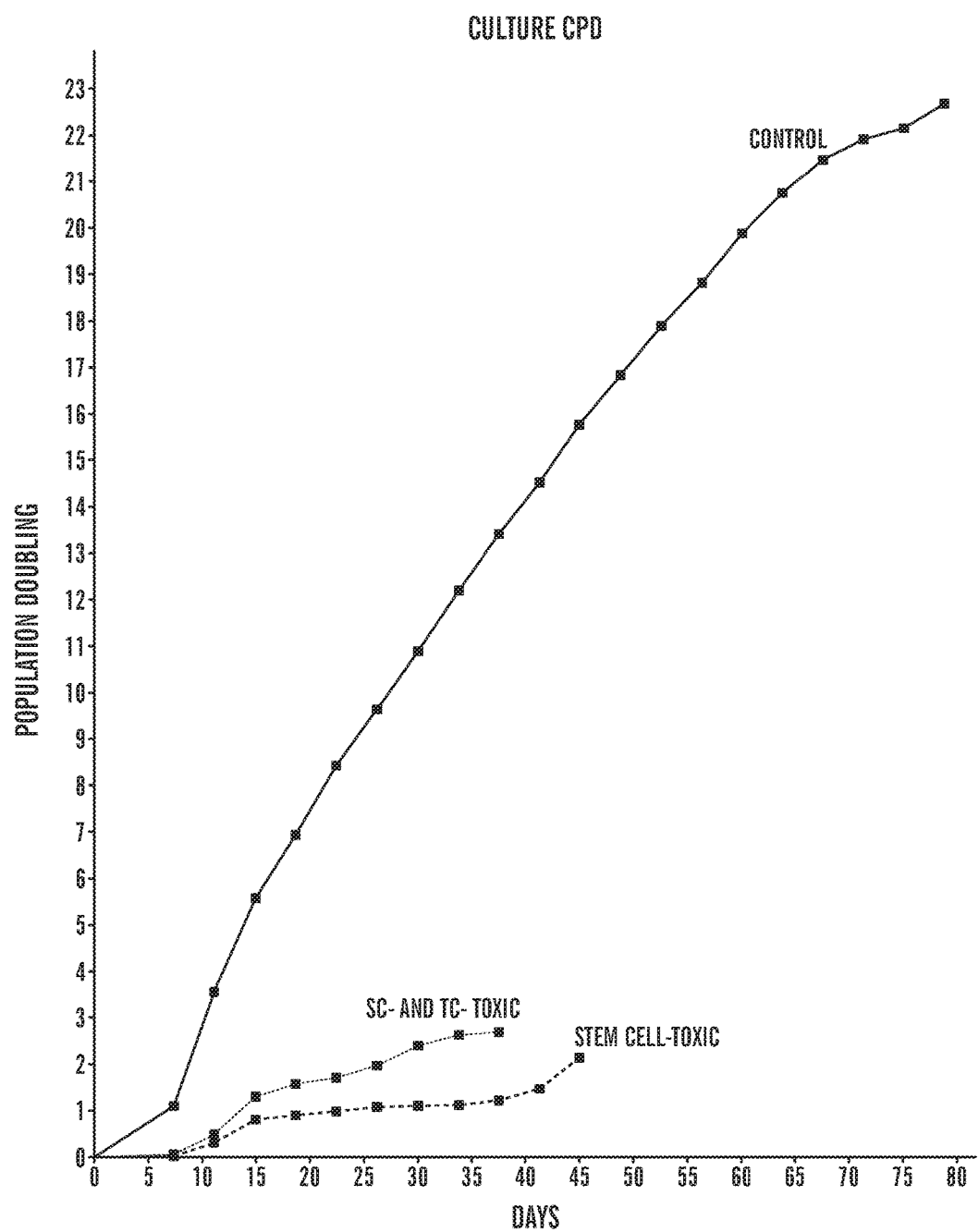
FIG. 10 shows a graph of a comparison of computer-simulated cell kinetics data for an untreated control serial culture, a serial culture treated with a tissue stem cell-specific toxic agent at its IC90, and a serial culture treated with an agent toxic for both transient cells and tissue stem cells at its IC90. CDP, cumulative population doublings.

FIG. 9 provides a comparison of the effect of an agent that has transient cell-specific toxicity to one that has tissue stem cell-specific toxicity, both at IC90. The distinction is very clear; and by comparison to the control culture, the signature of the transient cell-specific toxin is discernible. FIG. 10 show that the invention schedule can also delineate agents that are only toxic to tissue stem cells from ones that are toxic to both tissue stem cells and transient cells. The essential dependence on tissue stem cell dilution is manifest by the culture treated with the dual toxic agent exhibiting greater doubling times, which seems counter-intuitive. However, because the dual toxic agent reduces transient cell number, it also reduces the rate of tissue stem cell dilution. This counter effect leads to better overall culture growth compared to an agent that only kills tissue stem cells, even though with the same efficiency.

Figure 11:
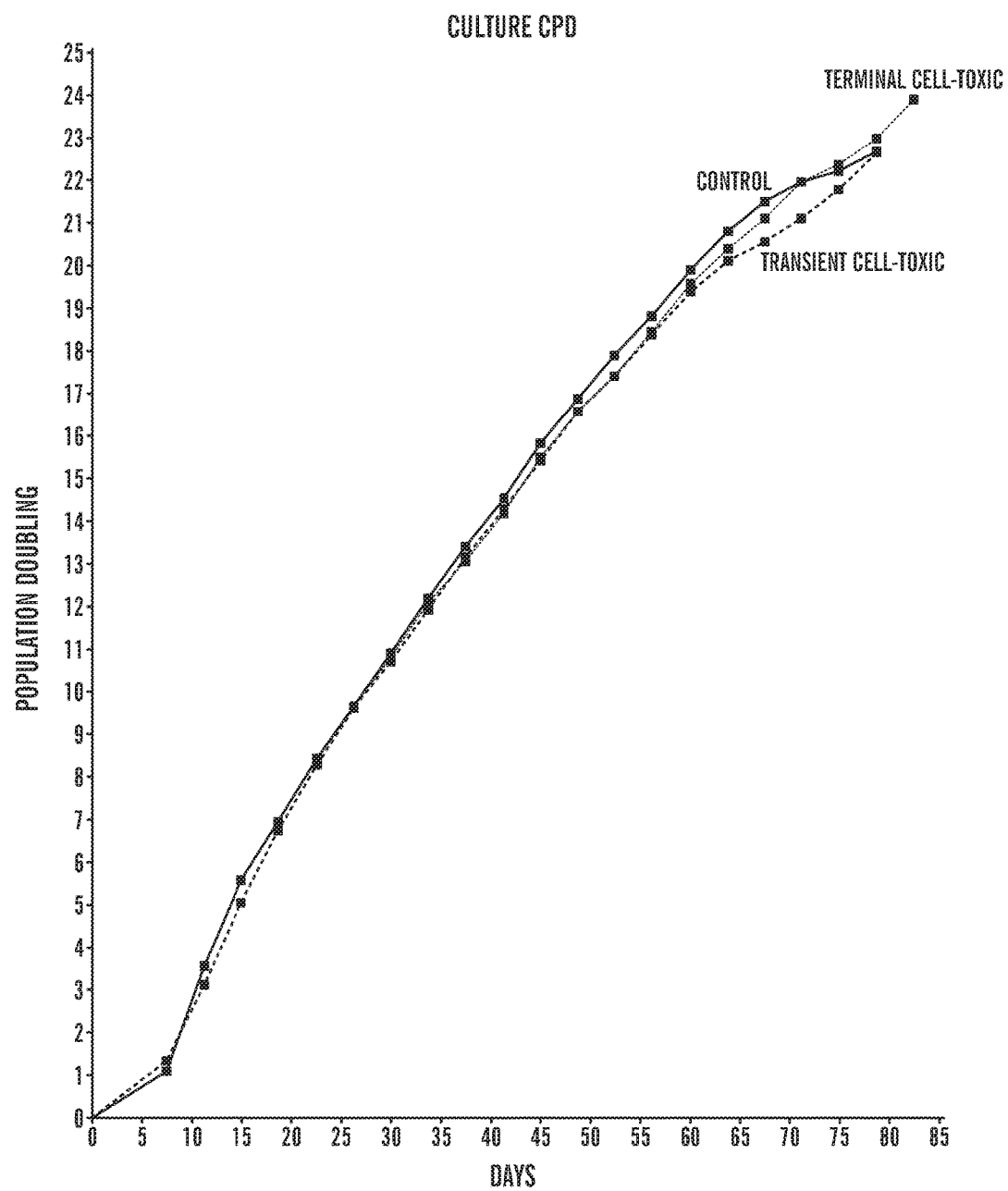
FIG. 11 shows a graph of a comparison of computer-simulated cell kinetics data for an untreated control serial culture, a serial culture treated with a transient cell-specific toxic agent at its IC90, and a serial culture treated with a terminal cell-specific toxic agent at its IC90. CDP, cumulative population doublings.
Figure 12:
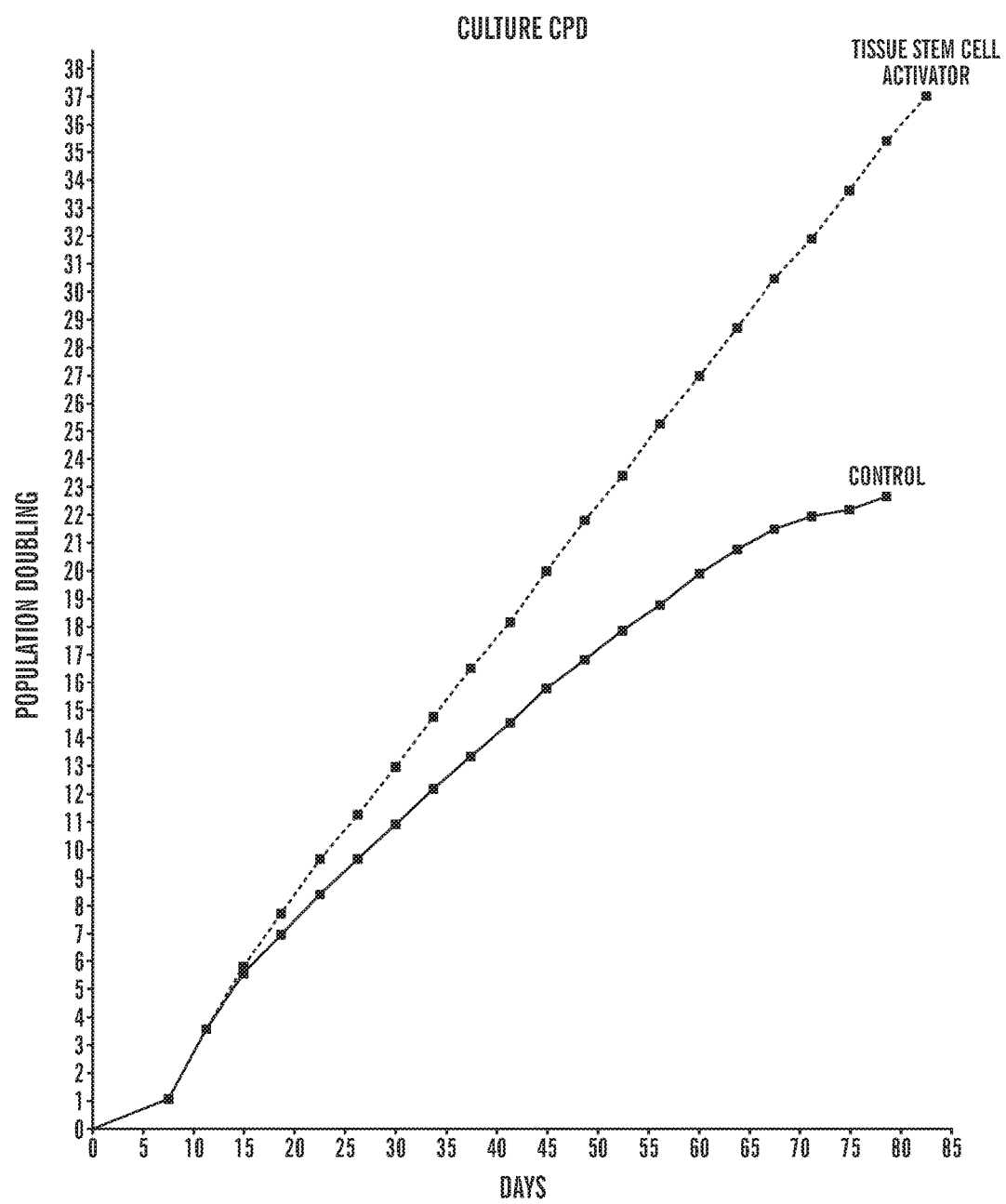
FIG. 12 shows a graph of a computer-simulation of the effect of a tissue stem cell-activating agent on the cumulative population doubling (CPD) output of the invention passage schedule for a human liver cell culture enriched for human liver stem cells. In the control condition, about 70% of human liver tissue stem cell divisions are asymmetric (as diagrammed in FIG. 1). Approximately 30% of the divisions are symmetric, producing two stem cells—and as a result no transient cells. The data shown simulate the effect of an agent that causes 70% of tissue stem cell divisions to become symmetric, with only 30% remaining asymmetric.
Figure 14A:
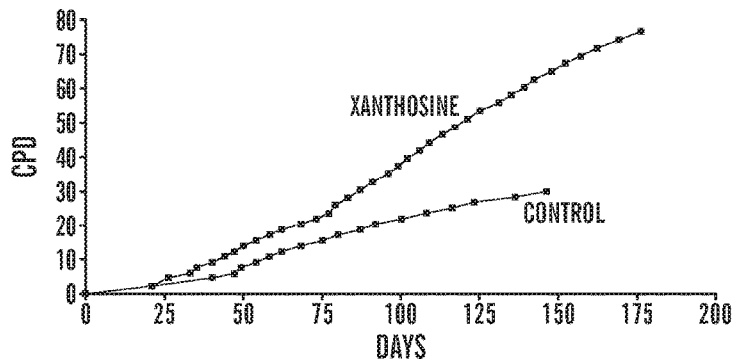
FIGS. 14A to 14D are graphs showing experimental and PSCK evaluation of the effect of xanthosine on the cell kinetics of human liver stem cell-enriched cultures.
Figure 14B:
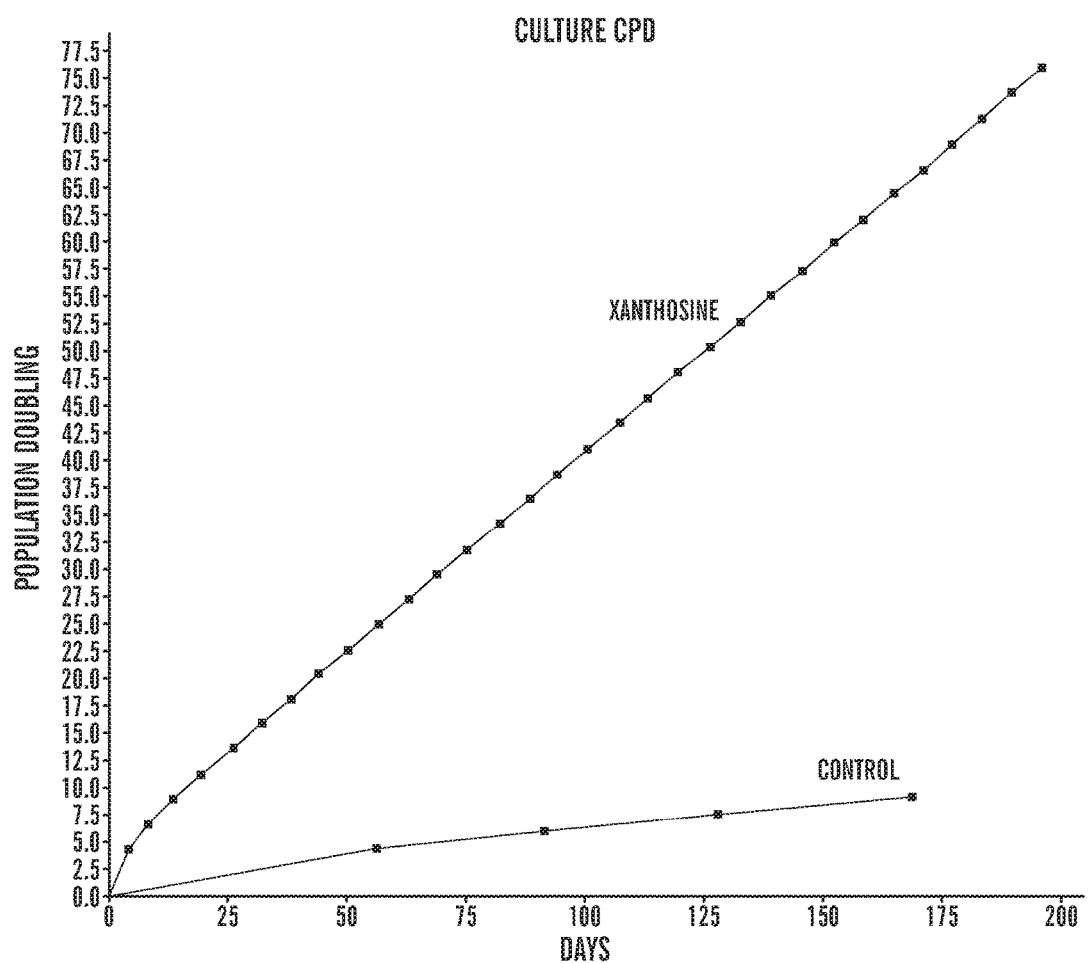
Figure 14C:
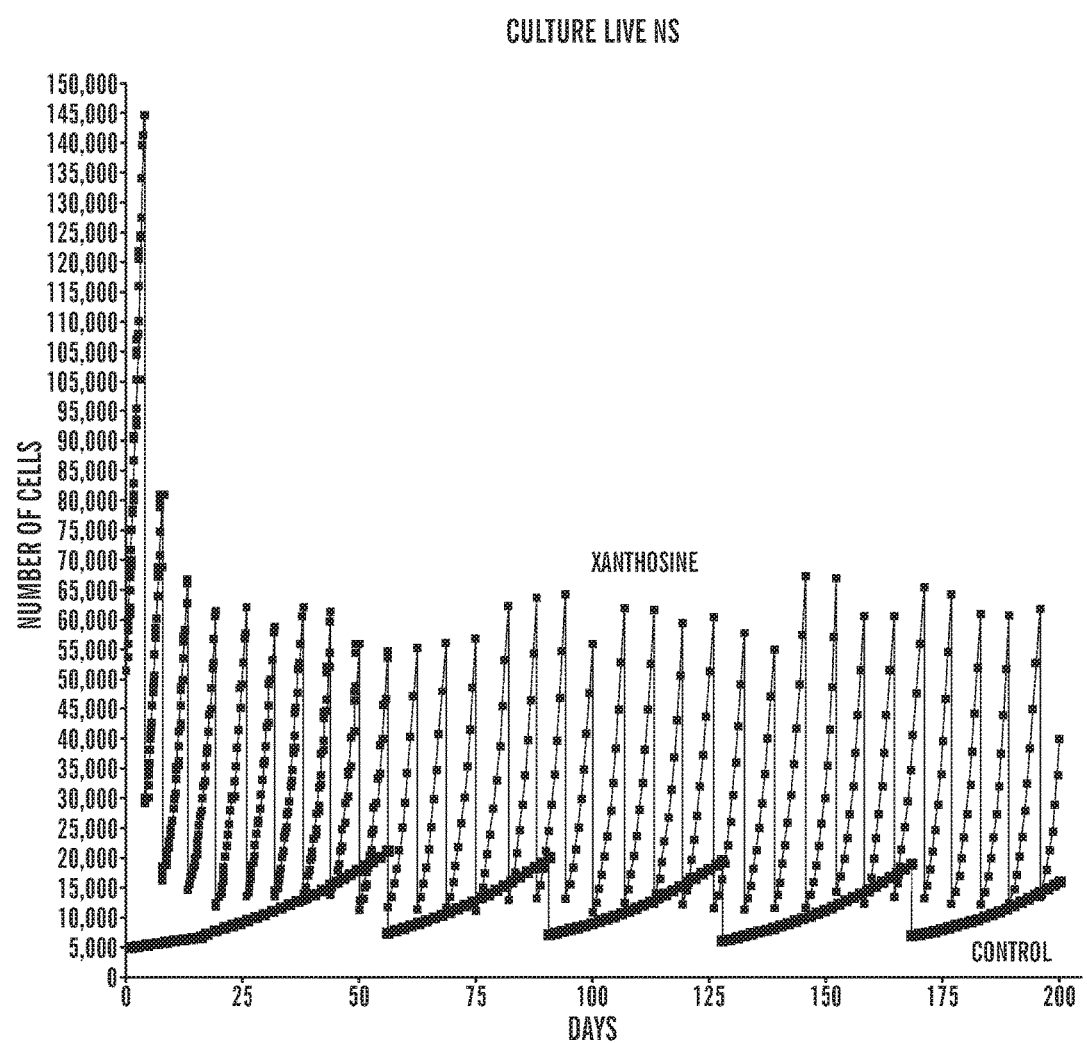
Figure 14D:
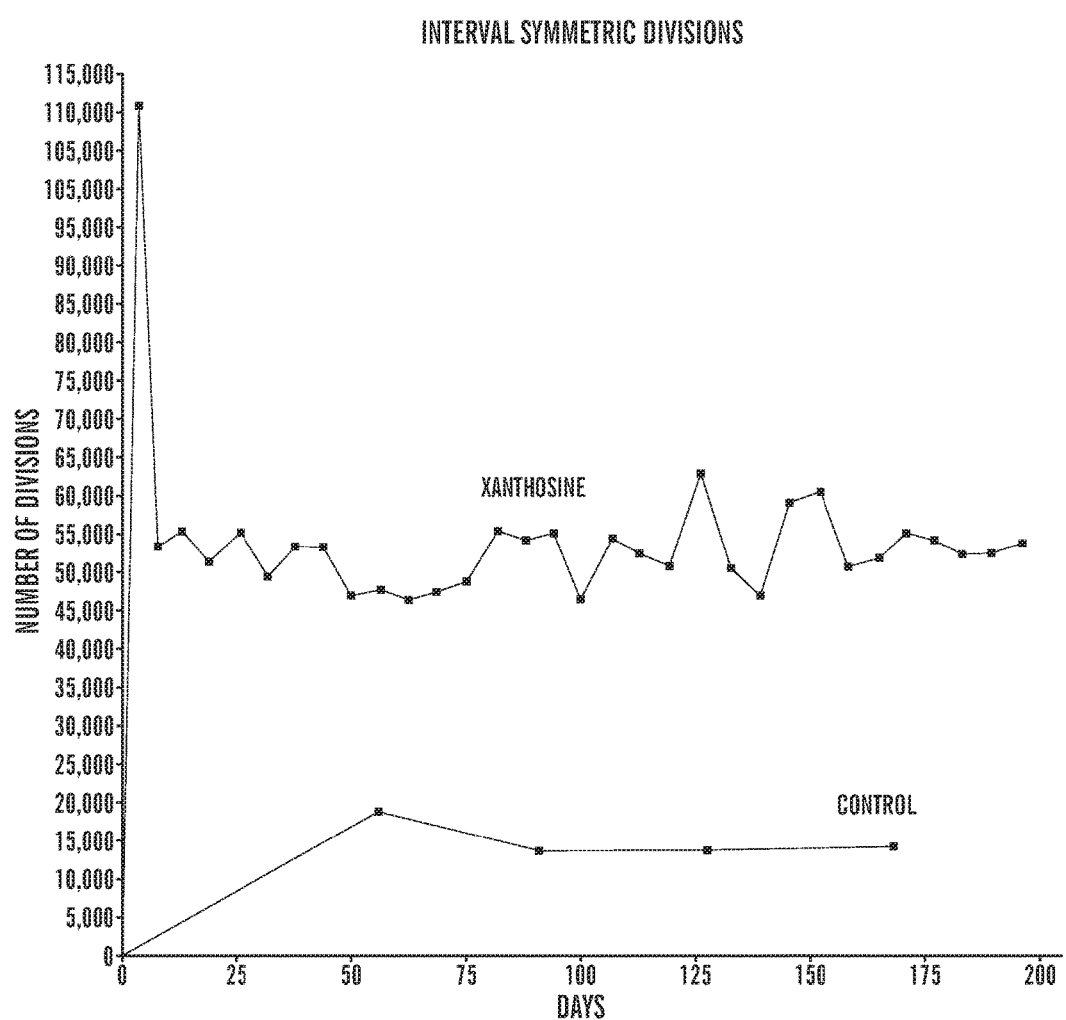
Figure 15A:
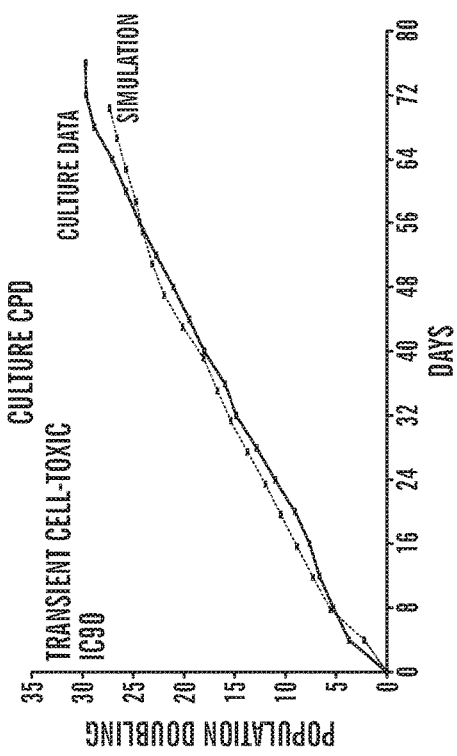
FIGS. 15A to 15D show PSCK simulation evaluation of cell type-specific toxic drug effects on serial passage CPD.
Figure 15B:
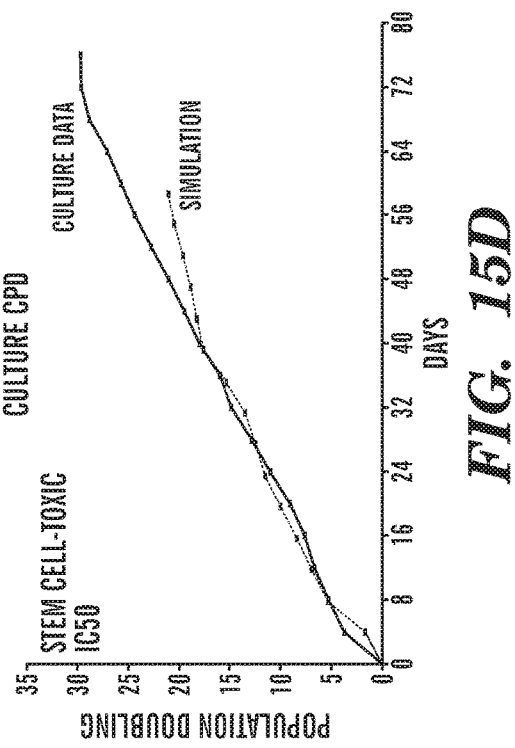
Figure 15C:
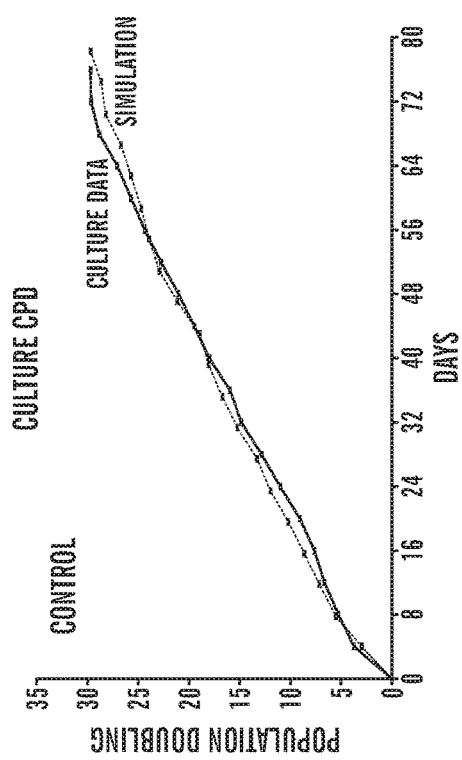
Figure 15D:
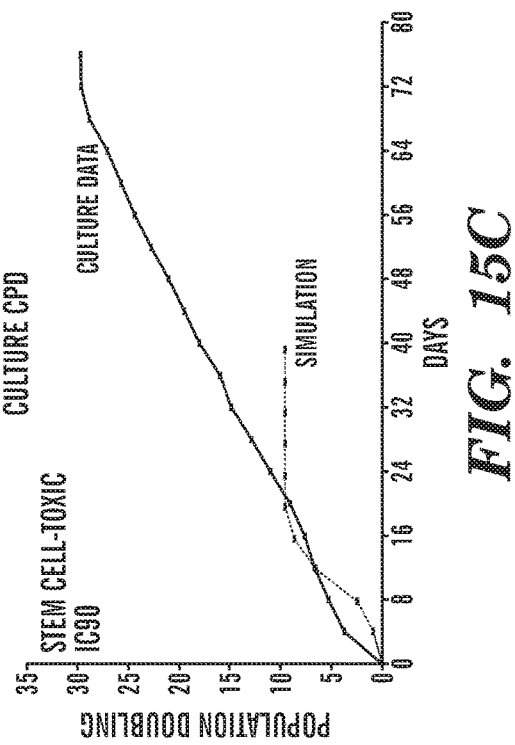
Figure 16B:
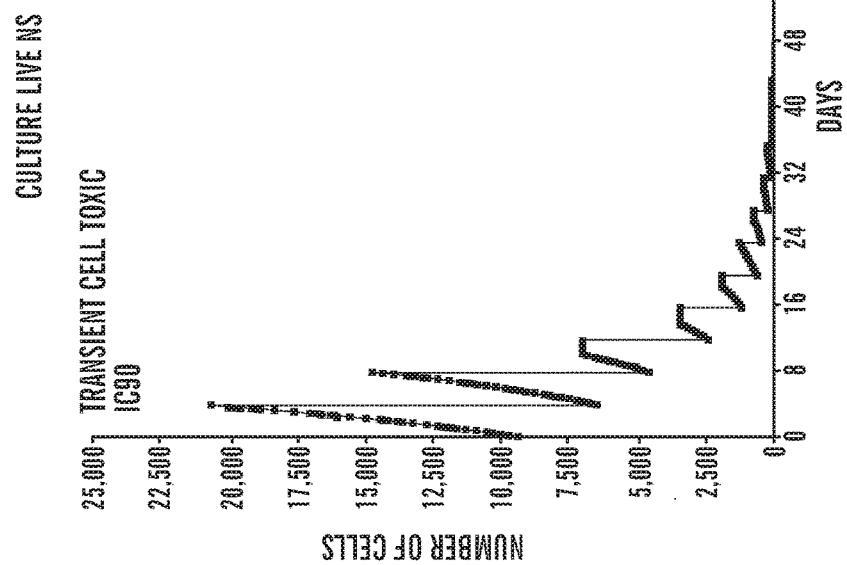
FIGS. 16A to 16D show live stem cell number deconstruction of the CPD simulations in FIG. 15.
Figure 16A:
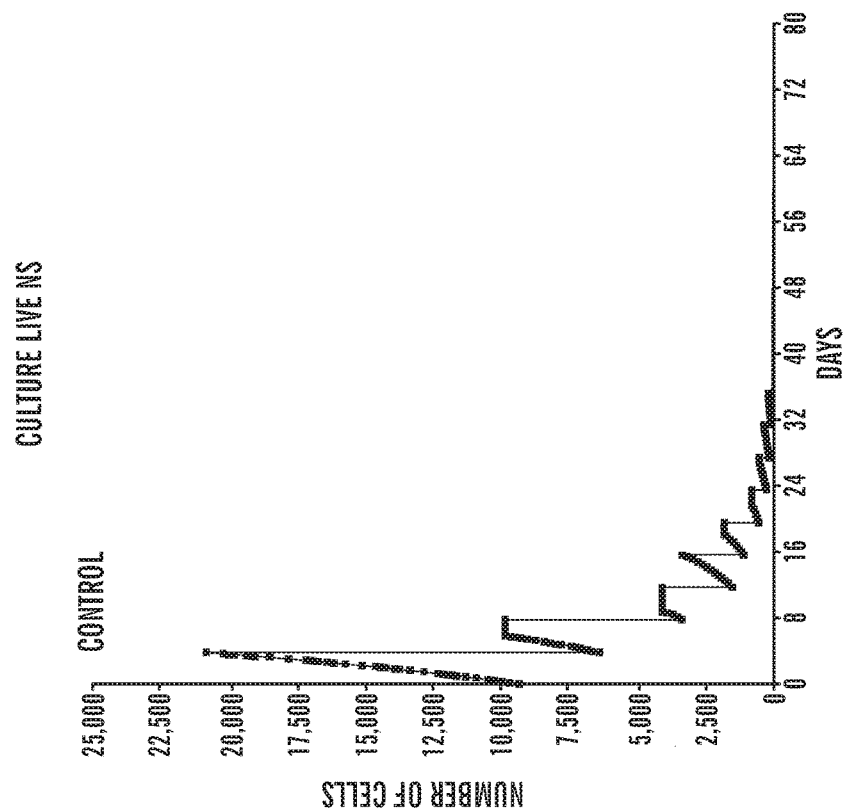
Figure 16D:
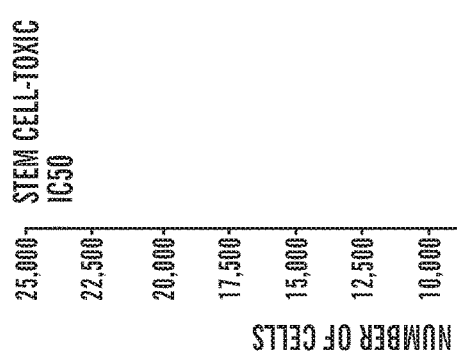
Figure 16C:

FIG. 11 shows that the invention schedule can also distinguish agents that have specific toxicity against terminally differentiated cells from those with specific toxicity against transient cells. In addition to a different pattern of deviation from the control signature, the culture treated with the terminal cell-specific toxin doubles to a higher value than the control. This counter-intuitive result is another positive overall growth effect that manifests a reduction in the rate of tissue stem cell dilution, in this case by eliminating terminal cells.

In each example, it is the innovation of evaluating cultures in a decline phase of the culture that allows these important distinctions to be made.

References Specification and Examples 1-2

1. Sherley, J. L. (2013) "New Cancer Diagnostics and Therapeutics From A 9th "Hallmark Of Cancer": Symmetric Self-Renewal By Mutated Distributed Stem Cells," Expert Rev. Mol. Diagn., 13, 797-810.
2. Rambhatla, L., Bohn, S. A., Stadler, P. B., Boyd, J. T., Coss, R. A., and Sherley, J. L. (2001) "Cellular Senescence: Ex vivo p53-Dependent Asymmetric Cell Kinetics," J. Biomed. Biotech. 1, 27-36.
3. Lee, H.-S., Crane, G. G., Merok, J. R., Tunstead, J. R., Hatch, N. L., Panchalingam, K., Powers, M. J., Griffith, L. G., and Sherley, J. L. (2003) "Clonal Expansion of Adult Rat Hepatic Stem Cell Lines by Suppression of Asymmetric Cell Kinetics (SACK)", Biotech. & Bioeng. 83, 760-771.
4. Paré, J.-F. and Sherley, J. L. (2006) "Biological Principles for Ex Vivo Adult Stem Cell Expansion," in Current Topics in Developmental Biology, ed. G. Schatten, Elsevier, Inc. (San Diego), Vol. 73, pp. 141-171.
5. Huh, Y. H., King, J., Cohen, J. and Sherley, J. L. (2011) "SACK-Expanded Hair Follicle Stem Cells Display Asymmetric Nuclear Lgr5 Expression with Non-Random Sister Chromatid Segregation," Sci. Rep. 1, 175; DOI: 10.1038/srep00176.
6. Paré, J.-F., and Sherley, J. L. (2011) "Culture Environment-Induced Pluripotency of SACK-Expanded Tissue Stem Cells," J. Biomed. and Biotechnol. vol. 2011, Article ID 312457, 12 pp., 2011. doi:10.1155/2011/312457.
7. Paré, J.-F., and Sherley, J. L. (2013) "Ex vivo Expansion of Human Pancreatic Distributed Stem Cells by Suppression of Asymmetric Cell Kinetics (SACK)," J. Stem Cell Res. & Therapy 3, 149. doi:10.4172/2157-7633.1000149.
8. Hayflick, L. (1965) "The Limited In Vitro Lifetime of Human Diploid Cell Strains," Exp. Cell Res. 37, 614-636.
9. Todaro, G. J. and Green, H. (1963) "Quantitative Studies of the Growth of Mouse Embryo Cells in Culture and Their Development into Established Lines," J. Cell Biol. 17, 299-313.

Example 3: Validation of the Use of Simulation Graphs Depicting Probabilistic Stem Cell Kinetics (PSCK) for Determining Toxicity of an Agent Against Stem Cells, and/or Transient Cells The methods described herein and computer simulations of probabilistic stem cell kinetics (PSCK) (FIGS. 1-12) have been validated for their ability to predict the cell multiplication output data of pre-senescent human lung cell cultures and expanded human liver cell strain cultures (FIGS. 13A-13D).

Using a pre-existing dataset developed with control human mini-tissue cultures and cultures treated with the purine nucleoside xanthosine as the test agent, we have validated the ability to use basic cell culture data, described in the methods herein, to detect effects on liver tissue stem cells. It is known in the art that xanthosine increases self-replication by adult tissue stem cells leading to their exponential expansion. We used xanthosine as the agent to expand human liver stem cell strains and to produce human liver mini-tissues. The FIGS. 14A to 14D depicts data of the cultures treated with xanthosine and demonstrates very clearly xanthosine's effect of inducing self-replication by liver tissue stem cells. Thus, culture systems of cells comprising heterogeneous cell population of stem, transient, and differentiated cells can be used to evaluate the activity of a test agent against tissue stem cells by using the methods described herein.

The methods described herein can accurately predict and quantify the tissue stem cell activity of drug candidates (test agents). The validation of the methods used to predict growth curves allows for assessment of the effect of an agent on the cells. The validation was performed against well-known serial culture data in the cell biology literature[8,9], existing human liver mini-tissue culture data, and recently developed human lung tissue cell culture data. The ability of computer software[10] to simulate the varied unspecified data sets is excellent. To obtain serial culture data specified to the inputs designed for the simulation, serial culture studies were conducted with a commercially available human lung cell strain that contains tissue stem cells (WI-38).[7,11] The supporting computer software provided an excellent simulation of the actual data obtained (See FIGS. 13 and 14). Thus, the methods and comparisons described herein can be used to accurately determine whether or not an agent is active against stem cells and/or transient cells and/or terminal cells in human culture. These data indicate that the technology can be applied to any tissue type having tissue stem cells, e.g. liver, lung, pancreas, heart, skin, etc. Positive or negative effects on cell growth can be determined.

Background

Because tissue stem cells are responsible for renewing and repairing human tissues, drugs that interfere with their function or cause their death are particularly toxic. FIG. 1 illustrates the universal, hierarchal human tissue cell kinetics architecture. Tissue stem cells (NS) subtend tissue turnover units comprised of many dividing and differentiating transient amplifying cells (NT) and terminally differentiated cells (NT-Terminal). As differentiated terminal cells age, expire, and are lost from their tissue, they are replaced by the division of transient cells, which are in turn replaced by the division of the resident tissue stem cells.

Despite the clear importance of tissue stem cells in adverse toxic drug effects, currently there are no pre-clinical assays for general tissue stem cell toxicity that do not require animals. Even animal testing is indirect, as it involves evaluating the pathological consequences of tissue stem cell toxicity (e.g., organ and tissue failure, cell hypoplasia, tissue dysplasia). Also, animal models are known to be poor predictors for cell toxicity in humans.[12] So, even laboratory animals are used as a last resort before initiating Phase I clinical trials for human drug safety evaluations.

A number of factors conspire to cause the current lack of direct pre-clinical assays for tissue stem cell toxicity. Because of their unique place in the universal cell kinetics hierarchy of human tissues, tissue stem cells are a minute fraction of any human tissue cell preparation. As a result, they have proven difficult to isolate in sufficient number or purity to establish reliable assays. For the same reason, biomarkers for tissue stem cells with sufficient specificity to quantify tissue stem cells for drug toxicity testing are still not readily available.[13]

The methods described herein circumvent these long-standing barriers of isolation and identification of tissue stem cells. It does so by exposing tissue stem cells directly to tested drugs in the context of fresh or limited-cultured human tissue cell preparations. The rate-limiting factor for the long-term cell production of any mammalian cell culture is directly related to the number, viability, and health of tissue stem cells in the culture. As shown in FIG. 1, since all transient cells progress ultimately to non-dividing terminal cells, continued cell production by any human cell culture absolutely depends on the continued presence of the proliferative function of tissue stem cells in the culture.

Because of the asymmetric self-renewal of tissue stem cells, if tissue cells are serially cultured, cell production eventually stops because of the inevitable dilution of the tissue stem cell number in the culture to zero.[1-7] Conventional serial culture involves growing a cell culture until the culture vessel is replete with cells. When replete, the cells are harvested; and a fixed fraction of the harvested cells is transferred to a new culture vessel. The new culture is allowed to grow until replete again, and the dilution process is performed again. There are well known examples of such serial culture schedules for both human cells[8] and rodent cells.[9] In the case of human tissue cell cultures, this serial process inevitably leads to a complete stoppage in new cell production. At this endpoint, the cultures contain only terminal cells. This outcome results first from dilution of tissue stem cell number to zero, followed by completion of the remaining transient cells differentiation and production of terminal cells.[7]

By altering the serial culture schedule, it is possible to relate the total cell output of a culture containing tissue stem cells to the relative number, viability, and quality of tissue stem cells present as they decline due to dilution. Herein, we employ a serial culture schedule that does not wait for cell cultures to become replete with cells. Instead, the specified schedule of culture dilutions is maintained no matter what cell number is obtained at the end of each culturing interval. Even when the cell number appears fixed, the dilution is continued until there are at least two successive culturing intervals without any increase in cell number. The cell kinetics of such a schedule can be related directly to the number, viability, and health of tissue stem cells during the duration of the serial culture. It can also be related to the cell kinetics activities of transient cells and terminal cells.

By comparing the cell kinetics (i.e., cumulative cell population doublings [CPD] versus time) of control cultures to drug-treated cultures, it is possible to determine whether an agent is toxic to tissue stem cells, transient cells, terminal cells, or any and all combinations of the three cell types. Conversely, it of course follows that the method can also identify agents that act on tissue stem cells, transient cells, or terminal cells to increase their division, viability, or function.

Validation Results

The PSCK modeling and computer simulation approach, as described herein in order to detect tissue stem cell toxicity, is based on the guiding principle that all primary human tissue cell cultures contain the three main cell kinetics categories of tissue cells, as illustrated in FIG. 1, which include rare tissue stem cells, abundant transient amplifying cells (which also include lineage-committed progenitor cells), and abundant terminally differentiated cells.

The PSCK simulation describes the progression of these cell kinetics relationships during serial passaging in culture prescribed by investigator-entered design variables. These design variables include cell kinetics factors for all three classes of cells, including their frequency, viability, and cell division rates, as well is passaging factors such as splitting basis and splitting interval. We employed multi-parameter fitting algorithm that allows us to find the set of design variables that provides the best simulation of experimental data sets. Once the design variables for the best-fit PSCK simulation are established, the PSCK software allows us to "deconstruct" specific quantitative information for each of the three cell kinetics types.

1. Validation of the PSCK Technology's Ability to Estimate Tissue Stem Cell Number FIG. 13 shows a comparison of the replicate WI-38 serial passage data (n=6) to their PSCK simulation. Importantly, the simulation models very well the characteristic variability of serial passage data. Although the six cultures were developed by ideal replicate sampling from a single initiating culture, their serial CPD data exhibit differences in slope and arrest times (FIG. 13A, arrow).

However, all show the culture arrest that is characteristic of all pre-senescent human tissue cultures (FIGS. 13A and 13C, arrows). The PSCK simulation captures this essential property with a high degree of confidence (Compare FIG. 13C to FIG. 13A).

FIG. 13D illustrates the special advantage of the PSCK software employed for quantitative analysis of the invention data. Each element of the simulation can be evaluated independently (i.e., "deconstructed"). Deconstruction provides an estimate of live tissue stem cell number at any time during serial culture. As predicted, the simulation shows that tissue stem cell number declines rapidly with serial culture, resulting in the arrest of the serial cultures.

2. Validation of the Invention's Ability to Detect the Effects of Stem Cell-Active Agents The ideally specified WI-38 study showed that the method of the invention could be employed to estimate stem cell number in serial cultures. The next important validation was to show that the invention could detect the effects of tissue stem cell-active agents. As an initial test of this ability, we used existing data sets from serial culture of our human liver stem cell strains.[14,15] Because these analyses were not ideally developed for the PSCK computer simulation format, they represented a more challenging validation.

The validation agent used was xanthosine, a purine nucleoside that we have shown independently to induce tissue stem cells to switch from asymmetric self-renewal divisions to symmetric divisions that lead to self-replication. The induced self-replication, which is reversed when xanthosine is removed, is the basis for our technology for producing human mini-tissues.[1,15] As shown in FIG. 14, although the unspecified data are not ideally simulated quantitatively, the PSCK simulation software captures the essential qualitative differences in the data sets (Compare FIG. 14B to 14A).

The control culture exhibits arrest after less than 30 population doublings, whereas the xanthosine-supplemented culture continues to exceed greater than 80 population doublings. Deconstruction of the simulation validates detection of the predicted increase in tissue stem cell number (FIG. 14C) as a result of increased symmetric self-replication divisions (FIG. 14D) in response to xanthosine.

The presented analysis of existing data from earlier xanthosine studies indicates that the method of the invention can be used to identify test agents active against tissue stem cells. We used the PSCK software[10] to simulate the predicted effects of toxic drugs on serial cultures of the human lung cells, which we have independently shown to contain asymmetrically self-renewing tissue stem cells.[7]

FIG. 15 shows four simulated conditions compared to the experimental mean CPD data developed in FIG. 13. Two idealized cell type-specific drugs were considered at their IC90. Compared to the control drug-free condition (FIG. 15A), a transient cell-specific toxic drug had modest effects on the long-term culture proliferative rate even at IC90 (FIG. 15B). In contrast, a stem cell-specific toxic drug, at its IC90, dramatically reduced the extent of culture proliferation (FIG. 15C). This effect was also detected at its IC50 (FIG. 15D).

Deconstruction analyses showed the specific effects on the two respective drug types on tissue stem cells (FIG. 16A to 16D). The transient cell-specific toxic drug at IC90 did not induce significant changes in live stem cell number (Compare FIG. 16B to 16A). However, both at IC90 (FIG. 16C) and IC50 (FIG. 16D), the tissue stem cell-specific toxic drug induced marked reductions in tissue stem cell number. These simulation analyses indicate that the method of the invention will have significant power to detect stem cell-specific toxic drug effects.

References Example 3

1. Lee, H.-S., Crane, G. G., Merok, J. R., Tunstead, J. R., Hatch, N. L., Panchalingam, K., Powers, M. J., Griffith, L. G., and Sherley, J. L. (2003) "Clonal Expansion of Adult Rat Hepatic Stem Cell Lines by Suppression of Asymmetric Cell Kinetics (SACK)", Biotech. & Bioeng. 83, 760-771.

2. Paré, J.-F. and Sherley, J. L. (2006) "Biological Principles for Ex Vivo Adult Stem Cell Expansion," in Current Topics in Developmental Biology, ed. G. Schatten, Elsevier, Inc. (San Diego), Vol. 73, pp. 141-171.

3. Huh, Y. H., King, J., Cohen, J. and Sherley, J. L. (2011) "SACK-Expanded Hair Follicle Stem Cells Display Asymmetric Nuclear Lgr5 Expression with Non-Random Sister Chromatid Segregation," Sci. Rep. 1,175. DOI: 10.1038/srep00176.

4. Paré, J.-F., and Sherley, J. L. (2011) "Culture Environment-Induced Pluripotency of SACK-Expanded Tissue Stem Cells," J. Biomed. and Biotechnol. vol. 2011, Article ID 312457, 12 pp., 2011. doi:10.1155/2011/312457.

5. Paré, J.-F., and Sherley, J. L. (2013) "Ex vivo Expansion of Human Pancreatic Distributed Stem Cells by Suppression of Asymmetric Cell Kinetics (SACK)," J. Stem Cell Res. & Therapy 3, 149. doi:10.4172/2157-7633.1000149.

6. http://asymmetrex.com

7. Rambhatla, L., Bohn, S. A., Stadler, P. B., Boyd, J. T., Coss, R. A., and Sherley, J. L. (2001) "Cellular Senescence: Ex vivo p53-Dependent Asymmetric Cell Kinetics," J. Biomed. Biotech. 1, 27-36.

8. Hayflick, L. (1965) "The Limited In Vitro Lifetime of Human Diploid Cell Strains," Exp. Cell Res. 37, 614-636.

9. Todaro, G. J. and Green, H. (1963) "Quantitative Studies of the Growth of Mouse Embryo Cells in Culture and Their Development into Established Lines," J. Cell Biol. 17, 299-313.

10. http://alphastarcorp.com/intro/indexjsp

11. Sherley, J. L., Stadler, P. B., and Johnson, D. R. (1995) "Expression of the Wild-type p53 Antioncogene Induces Guanine Nucleotide-Dependent Stem Cell Division Kinetics", Proc. Natl. Acad. Sci. 92, 136-140.

12. van Vliet, E. (2014) "Current Standing and Future Prospects for the Technologies proposed to Transform Toxicity Testing in the 21$^{st}$ Century," ALTEX 28, 17-44. DOI: 10.14573/altex.2011.1.017.

13. Sherley, J. L. (2013) "Advancing Renewable Normal Human Cell Assays for Drug Discovery," Drug Devel. Res., 74, 127-137.

14. http://www.kerafast.com/p-157-sack-xs-123-neonatal-human-liver-stem-cells.aspx 15. Sherley, J. L. and Panchalingam, K. (2010) "Methods for Ex Vivo Propagation of Adult Hepatic Stem Cells," U.S. Pat. No. 7,824,912 B2.

All references described herein are incorporated herein by reference in their entirety.

I claim:

1. An in vitro method of determining the effect of an agent on a heterogeneous population of cells comprising tissue stem cells, transient cells and terminally differentiated cells, comprising:

a. culturing a heterogeneous population of cells comprising tissue stem cells, transient cells and terminally differentiated cells,
b. contacting the cultured cells of step a) with an agent;
c. performing sequential passages of the cultured cells of step b) based on a specific time interval for passage rather than passage based on cell density, wherein the cells are sequentially passaged at the predetermined time interval using the same dilution factor at each passage such that the cells do not reach more than 50% confluency at the time for passage, and wherein the cells are sequentially passaged until at least two passages are performed without any increase in cell number in the culture prior to next passage;
d. determine the number of cells in the heterogeneous population at the time of each passage;
e. plotting the number of population doubling versus time of passage to obtain a growth curve for the heterogeneous population; and
f. comparing the growth curve of step e) to a control culture that has not been contacted with the agent of step b), wherein a deviation of the curve of step e) from the control indicates the agent has either a toxic or a positive effect on tissue stem cells, transient cells, or terminal cells.

2. The method of claim 1, wherein when the deviation of the curve is due to a lower amount of population doublings early in the growth curve and to a faster time to reach the two passages that are performed without any increase in cell number, the agent is toxic to tissue stem cells.

3. The method of claim 1, wherein when the deviation of the curve is due to a lower amount of population doublings late in the growth curve, and the time to reach the two passages that are performed without any increase in cell number in the culture is similar to the control, the agent is toxic to transient cells.

4. The method of claim 1, wherein when the deviation of the curve is due to a higher amount of population doublings in the middle of the growth curve, and the time to reach the least two passages that are performed without any increase in cell is similar to the control, the agent has a positive effect on tissue stem cells.

5. The method of claim 1, wherein the positive effect is an increase in tissue stem cell number, viability, or function.

6. The method of claim 1, wherein the toxic effect is a decrease in tissue stem cell number, viability, or function.

7. The method of claim 1, wherein there is a decline in the cell number of the culture at the time of passage, as compared to the cell number at the time of a prior passage, with six sequential passages.

8. The method of claim 1, wherein the period of time until at least two passages are performed without any increase in cell number in the culture is selected from the group consisting of less than 100 days, less than 90 days and less than 80 days.

9. The method of claim 1, wherein the heterogeneous population of cells cultured in step a) is cultured using a cell number selected from the group consisting of: less than 50,000 cells/cm$^2$; less than 10,000 cells/cm$^2$; and less than 7,000 cells/cm$^2$.

10. The method of claim 1, wherein the specific time interval is selected from the group consisting of: 108 hours; 96 hours; 72 hours; and 48 hours.

11. The method of claim 1, wherein the dilution factor is selected from the group consisting of: 1:2; 1:3; 1:4; and 1:10.

12. The method claim 1, wherein the percentage of tissue stem cells in the population is less than 5%.

13. The method of claim 1, wherein the cell number at the two passages that are performed without any increase in cell number has declined to a cell number that is selected from the group consisting of: less than 40% of the cell number in step a); less than 30% of the cell number in step a); less than 20% of the cell number in step a); less than 10% of the cell number in step a); and less than 5% of the cell number in step a).

14. An in vitro method of detecting the effect of an agent on a heterogeneous population of cells comprising tissue stem cells, transient cells and terminally differentiated cells, comprising:
   a. culturing a heterogeneous population of cells comprising tissue stem cells, transient cells and terminally differentiated cells,
   b. contacting the cultured cells of step a) with an agent;
   c. performing sequential passages of the cultured cells of step b) based on a specific time interval for passage rather than passage based on cell density, wherein the cells are sequentially passaged at the specific time interval using the same dilution factor at each passage such that the cells do not reach more than 50% confluency at the time for passage, and wherein the cells are sequentially passaged until at least two passages are performed without any increase in cell number in the culture prior to next passage;
   d. determine the number of cells in the heterogeneous population at the time of each passage;
   e. plotting the number of population doubling versus time of passage to obtain a growth curve for the heterogeneous population; and
   f. detecting the effect by comparing the growth curve of step e) to a control culture that has not been contacted with the agent of step b.

* * * * *